United States Patent
Okamoto et al.

(10) Patent No.: US 7,851,441 B2
(45) Date of Patent: Dec. 14, 2010

(54) WATER-SOLUBLE ELASTIN, PROCESS FOR PRODUCING SAME, AND FOOD AND MEDICINE CONTAINING SAME

(75) Inventors: Kouji Okamoto, Fukuoka (JP); Hiroshi Yamada, Fukuoka (JP); Iori Maeda, Fukuoka (JP)

(73) Assignee: Kyushu Institute of Technology, Fukuoka (JP)

( * ) Notice: Subject to any disclaimer, the term of this patent is extended or adjusted under 35 U.S.C. 154(b) by 649 days.

(21) Appl. No.: 11/666,443

(22) PCT Filed: Oct. 27, 2005

(86) PCT No.: PCT/JP2005/019751

§ 371 (c)(1),
(2), (4) Date: Apr. 27, 2007

(87) PCT Pub. No.: WO2006/046626

PCT Pub. Date: May 4, 2006

(65) Prior Publication Data

US 2008/0096812 A1 Apr. 24, 2008

(30) Foreign Application Priority Data

Oct. 29, 2004 (JP) ............... 2004-316584

(51) Int. Cl.
*A61K 38/39* (2006.01)
*C07K 14/78* (2006.01)
*C07K 1/14* (2006.01)

(52) U.S. Cl. ............. 514/12; 530/353; 530/422; 426/657

(58) Field of Classification Search .......... 514/12; 530/353, 422; 426/657
See application file for complete search history.

(56) References Cited

U.S. PATENT DOCUMENTS 4,419,288 A * 12/1983 Cioca .............. 530/353
7,125,960 B2 * 10/2006 Keiichi ............ 530/350

FOREIGN PATENT DOCUMENTS

| FR | 2 392 674 A | 12/1978 |
| FR | 2 498 452 A | 7/1982 |
| JP | 60-181005 A | 9/1985 |
| JP | 60-258107 A | 12/1985 |
| JP | 6-7092 A | 1/1994 |
| JP | 6-30616 B2 | 4/1994 |
| JP | 8-33661 A | 2/1996 |
| JP | 9-173361 A | 7/1997 |
| JP | 2002-205913 A | 7/2002 |
| JP | 2004-229611 A | 8/2004 |
| JP | 2005-13123 A | 1/2005 |
| JP | 2005-13124 A | 1/2005 |
| WO | 02/096978 A1 | 12/2002 |

OTHER PUBLICATIONS

B.C. Starcher, et al. "Coacervation and Ion-Binding Studies on Aortic Elastin", Biochimica et Biophysica Acta, 310 (1973) 481-486.
B.L. Rasmussen, et al. "A New Method for Purification of Mature Elastin", Analytical Biochemistry 64, 255-259 (1975).
Sekiya, Keizo; Okuda, Hiromichi, Inhibitory action of soluble elastin on thromboxane B2 formation in blood platelets, Biochimica.et. Biophysica.Acta., General Subjects (1984), 797(3), 348-53.
Kimura, Yoshiyuki; Okuda, Hiromichi, Inhibitory effects of soluble elastin on intraplatelet free calcium concentration, Thrombosis Research (1988), 52(1), 61-4.
The Japanese Biochemical Society, 'Shin Seikagaku Jikken Koza 1 Tanpakushitsu I-Bunri Seisei Seishitsu-', Dai 1 Pan, Dai 1 Satsu, 1990 Nen, Kabushiki Kaisha Tokyo Kagaku Dojin Hakko, pp. 143 to 152, vol. 1 (1990.

* cited by examiner

*Primary Examiner*—Chih-Min Kam
(74) *Attorney, Agent, or Firm*—Sughrue Mion, PLLC

(57) ABSTRACT

A low-molecular-weight water-soluble elastin having a molecular weight of about 10,000 to 30,000 and a high-molecular-weight water-soluble elastin having a molecular weight of about 30,000 to 300,000 are provided, 79% to 84% of the constituent amino acids of the elastin comprising proline, glycine, alanine, and valine, 2% to 3% comprising aspartic acid and glutamic acid, 0.7% to 1.3% comprising lysine, histidine, and arginine, and 0.2% to 0.4% comprising desmosine and isodesmosine. The low-molecular-weight water-soluble elastin that is obtained may be used in a functional food or a medicine. Such a high-purity water-soluble elastin may be produced by obtaining pure insoluble elastin by subjecting animal body tissue to a collagen removal treatment and then fragmenting the insoluble elastin by means of a solubilizing liquid. It may be produced simply, merely by adjusting the concentration of an alkaline solution and the reaction time without recovering insoluble elastin from the animal body tissue.

16 Claims, 11 Drawing Sheets

Figure 1:
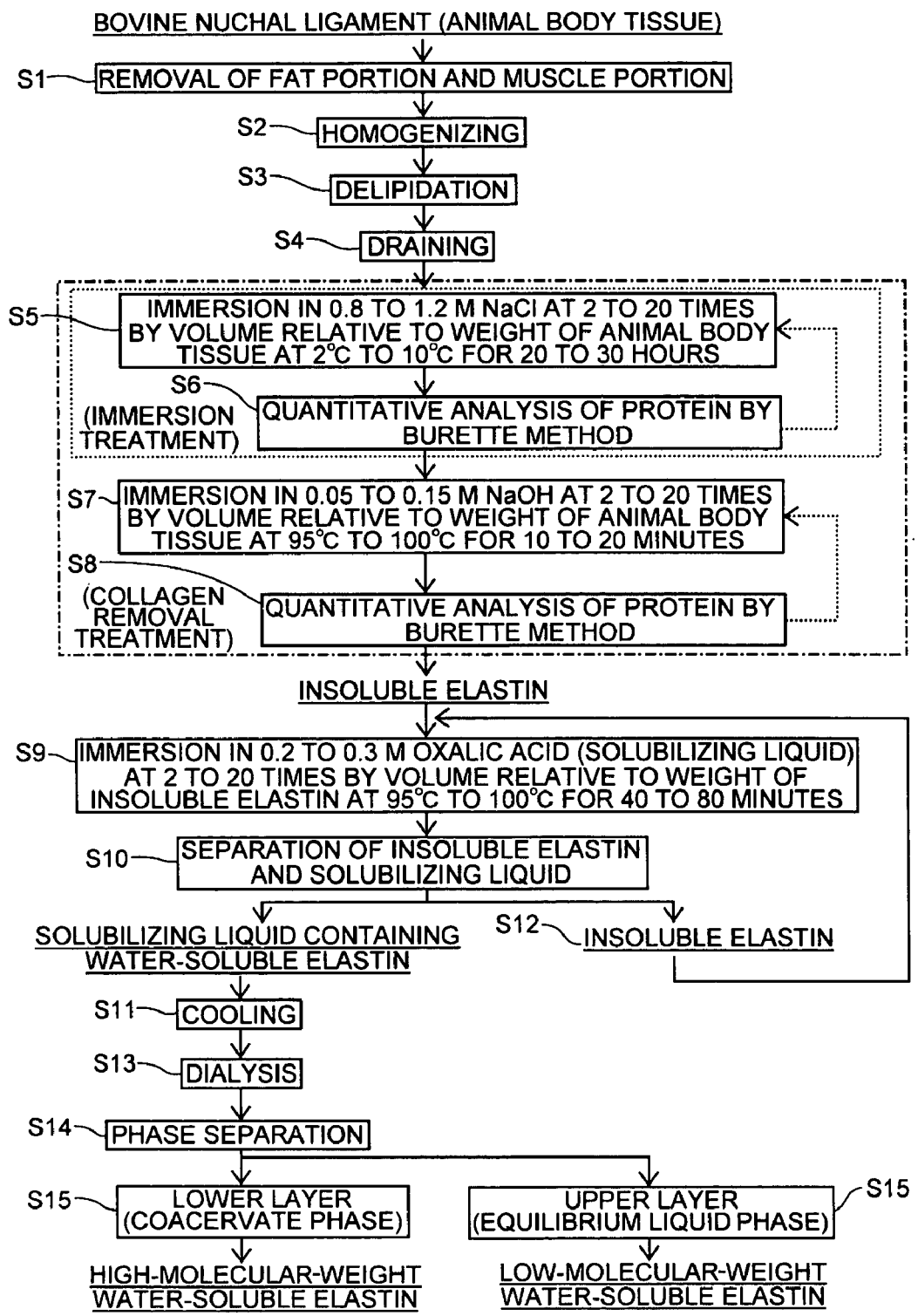

WATER-SOLUBLE ELASTIN, PROCESS FOR PRODUCING SAME, AND FOOD AND MEDICINE CONTAINING SAME

TECHNICAL FIELD

The present invention relates to a high-purity low-molecular-weight water-soluble elastin and a high-purity high-molecular-weight water-soluble elastin obtained from a water-soluble elastin, a process for producing them, and application of the low-molecular-weight water-soluble elastin to food and medicine.

BACKGROUND ART

Elastin is a protein that is present together with collagen in connective tissue such as the dermis, ligament, tendon, or vascular wall of animals, and in particular mammals. Elastin is normally present in vivo as an insoluble protein having a three-dimensional network structure. It is widely known that hydrolyzing such elastin with an acid or an alkali or treating it with an enzyme gives a water-soluble elastin. Since water-soluble elastin has the ability to retain a large amount of moisture, it is used in cosmetics, in particular as a moisturizing agent (e.g. Patent Publications 1 to 3), and also, together with collagen, as a health food due to cosmetic effects such as giving the skin elasticity (e.g. Patent Publications 4 to 6). Furthermore, it is anticipated that water-soluble elastin will be used in the field of regenerative medicine, such as artificial blood vessels (e.g. Patent Publications 7 to 10).

(Patent Publication 1) JP-A-60-258107 (JP-A denotes a Japanese unexamined patent application publication)

(Patent Publication 2) JP-A-60-181005

(Patent Publication 3) JP-A-2002-205913

(Patent Publication 4) JP-A-6-7092

(Patent Publication 5) JP-A-2005-13123

(Patent Publication 6) JP-A-2005-13124

(Patent Publication 7) JP-B-6-30616 (JP-B denotes a Japanese examined patent application publication)

(Patent Publication 8) JP-A-8-33661

(Patent Publication 9) JP-A-9-173361

(Patent Publication 10) WO 2002/96978

Various methods and means for obtaining water-soluble elastin have been proposed, but there is not yet an adequate method for obtaining a high-purity water-soluble elastin having an appropriate molecular weight. Elastin is extracted from the body tissue of an animal, and in this case it is usual to use animal body tissue that has been subjected to a pretreatment such as removal of unwanted portions or a delipidation operation. The pretreated tissue is dissolved in an acidic liquid containing formic acid or oxalic acid at a predetermined temperature or treated with an enzyme so as to fragment the insoluble elastin contained in the animal body tissue, thus giving a solubilizing liquid in which the water-soluble elastin is dissolved. However, in such a method, there is the problem that, in addition to elastin, collagen and other proteins contained in the animal body tissue are dissolved in the solubilizing liquid in which the water-soluble elastin has dissolved, and the purity of the water-soluble elastin that is finally obtained decreases. Moreover, because the water-soluble elastin that has dissolved in the solubilizing liquid has a high concentration in the solubilizing liquid or has been dissolved in the solubilizing liquid for a long time, the water-soluble elastin molecules might be cut up into low-molecular-weight polypeptides and lose the ability to coacervate in a low temperature zone (e.g. 35° C. to 40° C.). There is also the problem that elastin that has lost the ability to coacervate is not suitable for application in the field of medical materials, etc.

It has been reported that water-soluble α-elastin and β-elastin can be obtained by subjecting purified insoluble elastin to an extraction treatment with hot oxalic acid (Nonpatent Publication 1). However, the molecular weight of the α-elastin reported in Nonpatent Publication 1 is 70,000 and the molecular weight of the β-elastin is 10,000 or less, and these are different from those of the high-purity water-soluble elastin of the present invention, which will be described later. Patent Publication 1 above discloses that an insoluble elastin is decomposed by a protease to give a soluble elastin having a molecular weight of 15,000 to 300,000. However, this elastin has a very broad molecular weight range and contains fragments due to enzymatic decomposition, etc., and it seems unlikely that the purity will be high. Patent Publication 7 above reports that an insoluble elastin is decomposed with pepsin to give a water-soluble elastin having a molecular weight of 8,300 to 640,000, but this is unlikely to have a high purity judging from the amino acid composition (in particular, proline, glycine, alanine, valine). Furthermore, Patent Publication 10 above reports that a water-soluble elastin is obtained by treating an insoluble elastin with hot oxalic acid; it can be anticipated from the amino acid composition that this will have a high purity, and in this publication in order to obtain a biocompatible functional material the water-soluble elastin thus obtained is crosslinked. The amino acid composition of the purified insoluble elastin partially overlaps that of the high-purity water-soluble elastin of the present invention; it is reported to be formed from 80% to 83% proline, glycine, alanine, and valine, 2% to 3% aspartic acid and glutamic acid, 0.7% to 1.0% lysine, histidine, and arginine, and 0.3% to 0.4% desmosine and isodesmosine (e.g. Nonpatent Publication 2).

(Nonpatent Publication 1) Biochimica et Biophysica Acta, 310 (1973) 481-486

(Nonpatent Publication 2) Analytical Biochemistry, 64 (1975) 255-259

DISCLOSURE OF INVENTION

Problems to Be Solved by the Invention

It is an object of the present invention to provide a low-molecular-weight and high-purity water-soluble elastin that can be used as a functional food or a medicine, and a high-molecular-weight and high-purity water-soluble elastin that can be used as a cosmetic or a medical material. It is another object of the present invention to provide an industrial process for producing a high-purity water-soluble elastin.

Means for Solving the Problems

Among the present inventions, the invention according to Embodiment 1 is a low-molecular-weight water-soluble elastin having a molecular weight of about 10,000 to 30,000, 79% to 84% of the constituent amino acids of the elastin comprising proline, glycine, alanine, and valine, 2% to 3% comprising aspartic acid and glutamic acid, 0.7% to 1.3% comprising lysine, histidine, and arginine, and 0.2% to 0.4% comprising desmosine and isodesmosine. In the present invention, the aspartic acid content includes asparagine, and the glutamic acid content includes glutamine.

The invention according to Embodiment 2 is a high-molecular-weight water-soluble elastin having a molecular weight of about 30,000 to 300,000, 79% to 84% of the constituent amino acids of the elastin comprising proline, glycine, alanine, and valine, 2% to 3% comprising aspartic acid and glutamic acid, 0.7% to 1.3% comprising lysine, histidine, and arginine, and 0.2% to 0.4% comprising desmosine and isodesmosine.

The invention according to Embodiment 3 is a process for producing the water-soluble elastin according to Embodiment 1 or 2. That is, with regard to a process for producing a water-soluble elastin from animal body tissue, the process for producing a water-soluble elastin comprises (1) a step of obtaining an insoluble elastin by subjecting animal body tissue to a collagen removal treatment, (2) a step of obtaining a dissolved-elastin solubilizing liquid by dissolving the insoluble elastin in a solubilizing liquid, and (3) a step of separating the dissolved-elastin solubilizing liquid into two layers by a phase separation operation, recovering a low-molecular-weight water-soluble elastin from the upper layer, and recovering a high-molecular-weight water-soluble elastin from the lower layer.

The invention according to Embodiment 8 relates to another process for producing the water-soluble elastin according to Embodiment 1 or 2. That is, with regard to a process for producing a water-soluble elastin from animal body tissue, the process for producing a water-soluble elastin comprises (1) a step of pretreating animal body tissue, (2) a step of carrying out an alkali extraction by immersing the pretreated animal body tissue in an alkaline solution and removing a solution containing collagen and other unwanted protein extracted from the animal body tissue, (3) a step of carrying out alkali dissolution by dissolving the animal body tissue residue after repeating the operation of (2) above so as to recover a solution containing a freed water-soluble elastin, and (4) a step of separating the solution containing the water-soluble elastin recovered in the alkali dissolution step into two layers by a phase separation operation, recovering a low-molecular-weight water-soluble elastin from the upper layer, and recovering a high-molecular-weight water-soluble elastin from the lower layer.

Furthermore, the invention according to Embodiment 12 is a functional food comprising a low-molecular-weight water-soluble elastin having a molecular weight of about 10,000 to 30,000, 79% to 84% of the constituent amino acids of the elastin comprising proline, glycine, alanine, and valine, 2% to 3% comprising aspartic acid and glutamic acid, 0.7% to 1.3% comprising lysine, histidine, and arginine, and 0.2% to 0.4% comprising desmosine and isodesmosine.

The invention according to Embodiment 14 is a medicine having as an active ingredient a low-molecular-weight water-soluble elastin having a molecular weight of about 10,000 to 30,000, 79% to 84% of the constituent amino acids of the elastin comprising proline, glycine, alanine, and valine, 2% to 3% comprising aspartic acid and glutamic acid, 0.7% to 1.3% comprising lysine, histidine, and arginine, and 0.2% to 0.4% comprising desmosine and isodesmosine.

As an invention related to a specific application of the medicine according to Embodiment 14, the invention according to Embodiment 16 is an antiarteriosclerotic agent, the invention according to Embodiment 17 is a lipidosis improving agent, and the invention according to Embodiment 18 is an antithrombogenic agent.

Effects of Invention

In accordance with the present invention, there are provided a low-molecular-weight and high-purity water-soluble elastin having a molecular weight of about 10,000 to 30,000, and a high-molecular-weight and high-purity water-soluble elastin having a molecular weight of about 30,000 to 300,000. Since the low-molecular-weight water-soluble elastin of the present invention has high digestive absorption, it can be used as a functional food or a medicine. Furthermore, the high-molecular-weight water-soluble elastin can be used as a cosmetic or a medical material.

Moreover, in accordance with the present invention, there is provided an industrially advantageous process for producing the water-soluble elastin. In the process according to Embodiment 3, an insoluble elastin is first produced in a high purity state by carrying out a collagen removal treatment in which collagen is removed from animal body tissue. That is, by first carrying out a treatment that emphasizes removal of collagen contained in animal body tissue, the majority of the remaining animal body tissue components can be turned into a high purity insoluble elastin that contains no collagen, which becomes a contaminant during purification of a water-soluble elastin. Therefore, in subsequent steps, even if the remaining animal body tissue is immersed in a solubilizing liquid, although the insoluble elastin is fragmented to become a water-soluble elastin, which is freed and dissolves in the solubilizing liquid, collagen is not leached, and it is therefore possible to produce a high-purity water-soluble elastin having few contaminants.

Furthermore, in the process according to Embodiment 8, which is another production process, the alkali extraction step and alkali dissolution step, in which animal body tissue is immersed in an alkaline solution, carry out in one operation a collagen removal treatment, a treatment to remove unwanted protein other than collagen, and a treatment to fragment/solubilize insoluble elastin, and it is therefore possible to shorten the treatment time by recovering high-purity water-soluble elastin without purifying insoluble elastin in animal body tissue.

BRIEF DESCRIPTION OF DRAWINGS (FIG. 1) A flow diagram showing a process for producing a water-soluble elastin (invention of Embodiment 3).

(FIG. 2) A flow diagram showing a process for producing a water-soluble elastin (invention of Embodiment 8).

(FIG. 3) A diagram showing change in total serum cholesterol.

(FIG. 4) A diagram showing change in LDL-cholesterol.

(FIG. 5) A diagram showing change in HDL-cholesterol.

(FIG. 6) A diagram showing change in triglyceride.

(FIG. 7) A diagram showing change in lipid peroxide.

(FIG. 8) A diagram showing change in vascular elastic modulus.

(FIG. 9) A diagram showing the state of the inner membrane surface of a blood vessel on the blood flow side.

Figure 10:
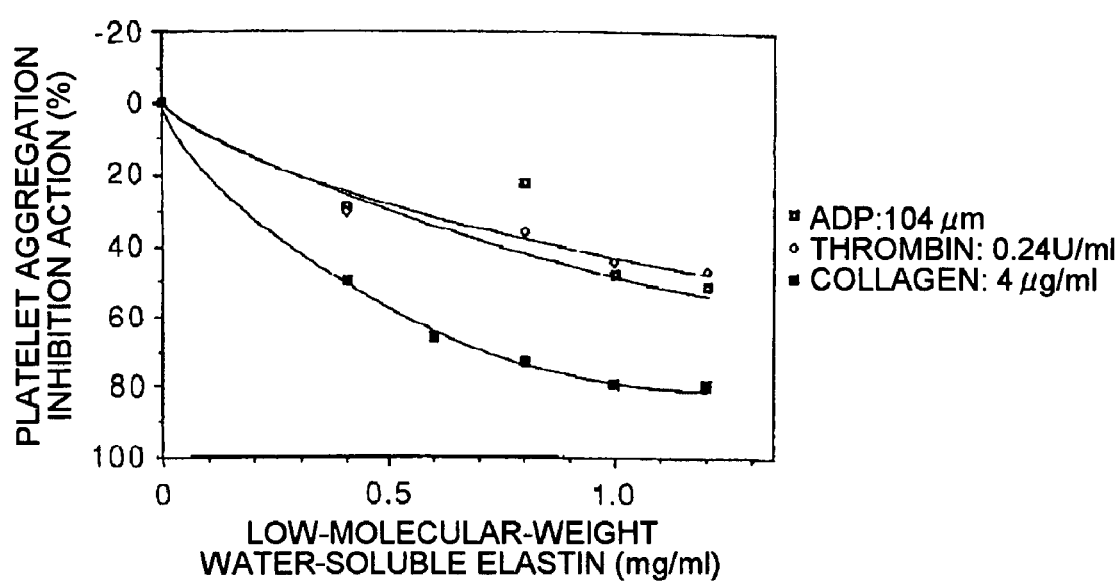

(FIG. 10) A diagram showing platelet aggregation inhibition action.

Figure 11:
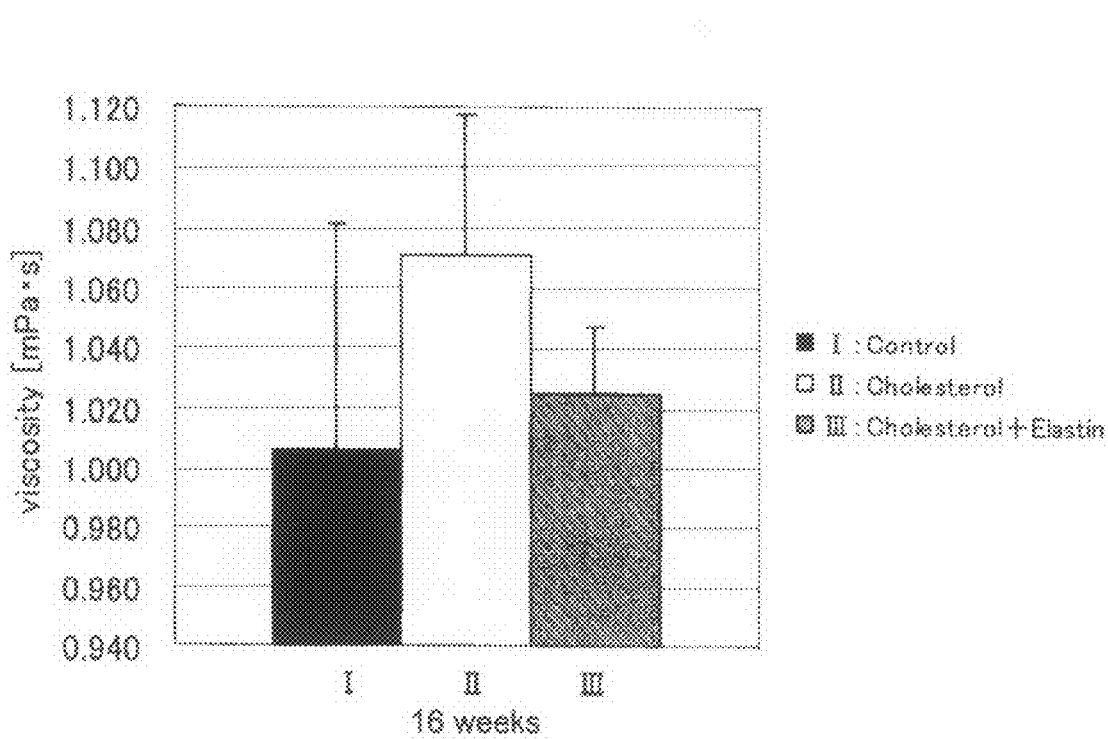

(FIG. 11) A diagram showing viscosity in blood.

BEST MODE FOR CARRYING OUT THE INVENTION

The water-soluble elastin of the present invention is a low-molecular-weight water-soluble elastin having a molecular weight of about 10,000 to 30,000 and a high-molecular-weight water-soluble elastin having a molecular weight of about 30,000 to 300,000, 79% to 84% of the constituent amino acids of the elastin comprising proline, glycine, alanine, and valine, 2% to 3% comprising aspartic acid and glutamic acid, 0.7% to 1.3% comprising lysine, histidine, and arginine, and 0.2% to 0.4% comprising desmosine and isodesmosine. The amino acid composition of purified insoluble elastin is 80% to 83% proline, glycine, alanine, and valine, 2% to 3% aspartic acid and glutamic acid, 0.7% to 1.0% lysine, histidine, and arginine, and 0.3% to 0.4% desmosine and isodesmosine, and since the amino acid composition of the water-soluble elastin of the present invention is mostly close to the above, it can be said that it has high purity. When elastin is subjected to an amino acid analysis, hydrolysis is usually carried out with 6 N hydrochloric acid for at least 48 hours, and since Asn is converted into Asp and Gln is converted into Glu, the value for Asp is expressed as the total of Asp+Asn, and the value for Glu is expressed as the total of Glu+Gln. In the amino acid composition of the present invention also, the content of aspartic acid is defined as including the original asparagine, and the content of glutamic acid as including the original glutamine.

The high-purity water-soluble elastin of the present invention may be produced by the two processes below. The first process is the process according to Embodiment 3. That is, with regard to a process for producing a water-soluble elastin from animal body tissue, the process comprises (1) a step of obtaining an insoluble elastin by subjecting animal body tissue to a collagen removal treatment, (2) a step of obtaining a dissolved-elastin solubilizing liquid by dissolving the insoluble elastin in a solubilizing liquid, and (3) a step of separating the dissolved-elastin solubilizing liquid into two layers by a phase separation operation, recovering a low-molecular-weight water-soluble elastin from the upper layer, and recovering a high-molecular-weight water-soluble elastin from the lower layer.

The animal body tissue is not particularly limited, but it is preferable to use nuchal ligament or aorta obtained from a mammal such as a pig, a horse, a cow, or a sheep since the elastin content is high. The animal body tissue may first be homogenized using a homogenizer. Homogenizing may be carried out using equipment such as a mixer or a meat chopper, which finely cuts the animal body tissue, preferably into pieces of 3 mm square or less, and more preferably into a paste. It is preferable for the finely cut animal body tissue to have a smaller particle size since the efficiency of removing collagen and other unwanted protein can be improved. The homogenized animal body tissue may be subjected to a delipidation treatment by, for example, boiling it in hot water or hot dilute aqueous alkaline solution or treating it with an organic solvent.

As a method for obtaining an insoluble elastin by removing collagen from animal body tissue, in relation to step (1) of the first process above, it is preferable to remove collagen with an alkaline solution. In particular, it is preferable to employ a treatment method in which animal body tissue is immersed in an alkaline solution containing, per L of solution, 0.05 to 0.5 mol of one or more alkali compounds selected from the group consisting of sodium hydroxide, potassium hydroxide, calcium hydroxide, and barium hydroxide, preferably 0.05 to 0.3 mol, and more preferably 0.05 to 0.15 mol, at 90° C. to 105° C., and preferably 95° C. to 100° C., for 10 to 20 minutes (Embodiment 4).

The insoluble elastin may be fragmented and freed by an alkaline solution, as well as by an acidic solution, to become a water-soluble elastin, which can be dissolved, but conditions such as alkaline solution concentration, temperature, and treatment time of the above-mentioned collagen removal treatment operation are defined so that the collagen is leached before the insoluble elastin is fragmented so as to become a water-soluble elastin and is freed and dissolved. By treatment under the above-mentioned conditions, collagen in the animal body tissue can therefore be leached efficiently into alkaline solution and removed, and as a result a high-purity insoluble elastin can be obtained. This alkaline solution in the collagen removal treatment has an effect in both extracting and removing collagen and removing unwanted protein other than collagen.

Such a collagen removal treatment may be repeated a plurality of times until the concentration of protein leached into a filtrate obtained by filtering insoluble elastin from the alkaline solution becomes a predetermined value or less. Hardly any fragmentation of the insoluble elastin occurs even if the collagen removal treatment is carried out repeatedly until the concentration of leached protein (that is, the concentration of collagen, etc. that has been leached) becomes a predetermined concentration as long as the treatment is carried out under the above-mentioned conditions. By repeatedly carrying out the collagen removal treatment, it is therefore possible to produce a water-soluble elastin having a higher degree of purification than in the case in which the collagen removal treatment is carried out only once.

Furthermore, in the first process, prior to the collagen removal treatment, an immersion treatment may be carried out in which animal body tissue is immersed in a salt solution containing, per L of solution, 0.1 to 2 mol of one or more salts selected from the group consisting of sodium chloride, potassium chloride, calcium chloride, and barium chloride, and preferably 0.8 to 1.2 mol, at 2° C. to 10° C. for 12 to 48 hours, and preferably 20 to 30 hours (Embodiment 5). Such a salt solution treatment may be carried out a plurality of times, and this treatment enables unwanted protein other than collagen to be removed in advance.

With regard to a method for obtaining a dissolved-elastin solubilizing liquid by dissolving the insoluble elastin obtained in step (1) above in a solubilizing liquid, in relation to step (2) of the first process, there are cases in which an acidic solution is used as a solubilizing liquid and cases in which an alkaline solution is used.

A preferred acidic solution is an acidic solution containing, per L of solution, 0.1 to 0.5 mol of one or more acid compounds selected from the group consisting of oxalic acid, formic acid, acetic acid, succinic acid, malic acid, tartaric acid, citric acid, benzoic acid, betaine, difluoroacetic acid, trifluoroacetic acid, phosphoric acid, sulfamic acid, perchloric acid, and trichloroacetic acid, and preferably 0.2 to 0.3 mol, at a solution temperature of 90° C. to 105° C., and preferably 95° C. to 100° C. (Embodiment 6). Such conditions are appropriate for producing a water-soluble elastin from an insoluble elastin as well as for avoiding cutting up the water-soluble elastin molecules that have been freed and dissolved in the solubilizing liquid, and it is therefore possible to produce a water-soluble elastin having a sufficient molecular weight. The treatment time for solubilization is 20 to 120 minutes, and preferably 40 to 80 minutes. If insoluble elastin remains, the insoluble elastin is immersed again in a fresh acidic solution, and treatment with this acidic solution is repeated until the insoluble elastin dissolves completely.

A preferred alkaline solution is an alkaline solution containing, per L of solution, 0.05 to 0.5 mol of one or more alkali compounds selected from the group consisting of sodium hydroxide, potassium hydroxide, calcium hydroxide, and barium hydroxide, and preferably 0.05 to 0.3 mol, at a solution temperature of 90° C. to 105° C., and preferably 95° C. to 100° C. (Embodiment 7). Such conditions are appropriate for producing a water-soluble elastin from an insoluble elastin as well as for avoiding cutting up the water-soluble elastin molecules that have been freed and dissolved in the solubilizing liquid, and it is therefore possible to produce a water-soluble elastin having a sufficient molecular weight. The treatment time for solubilization is 20 to 120 minutes, and preferably 40 to 80 minutes. If insoluble elastin remains, the insoluble elastin is immersed again in a fresh alkaline solution, and treatment with this alkaline solution is repeated until the insoluble elastin dissolves completely. When an alkaline solution is used as the solubilizing liquid, the alkaline solution used for the collagen removal treatment may be used continuously as the solubilizing liquid, and in this case the production cost can be reduced.

In a method for subjecting the dissolved-elastin solubilizing liquid obtained in step (2) above to phase separation and recovering each of the separated two layers, in relation to step (3) of the first process, a low-molecular-weight water-soluble elastin is recovered from the separated upper layer, and a high-molecular-weight water-soluble elastin is recovered from the separated lower layer. The properties of the water-soluble elastins thus obtained are explained in detail later.

FIG. 1 shows a flow diagram for when a water-soluble elastin is produced by the first process. The explanation below is given with reference to FIG. 1. The treatment conditions, etc. in FIG. 1 are shown as one example of the present invention.

Bovine nuchal ligament is used as the animal body tissue, attached portions having a low elastin content such as fat and muscle are scraped off using a knife, etc. (step S1), and the animal body tissue is homogenized using a homogenizer (step S2). Homogenizing may employ equipment such as a mixer or a meat chopper that can finely cut animal body tissue, preferably into pieces of 3 mm square or less, and more preferably into a paste. The smaller the particles of finely cut animal body tissue, the higher the efficiency of removing unwanted protein.

The homogenized animal body tissue is placed in at least 2 times by volume of boiling water (90° C. to 105° C., and preferably 95° C. to 100° C.) relative to the weight of the animal body tissue (2 mL per g of weight), and preferably 2 to 20 times by volume, boiled for 30 to 120 minutes, and preferably 60 to 120 minutes for delipidation (step S3), and drained (step S4). The draining referred to here does not specifically mean water alone, but means that liquid attached to the animal body tissue is drained. Delipidation is not sufficient when the delipidation time is less than 30 minutes, and it cannot be expected that carrying out delipidation for longer than 120 minutes would increase the delipidation effect any further. The delipidation efficiency may be enhanced by adding a total amount of 0.01 mol to 0.1 mol of at least any one of sodium hydroxide, potassium hydroxide, calcium hydroxide, and barium hydroxide relative to 1 L of boiling water, and the delipidation time may be shortened to 10 to 60 minutes. The delipidation operation is not limited to a method employing boiling water, and may employ an organic solvent generally used for the purpose of lipid extraction such as acetone, an ether, hexane, butanol, chloroform, or methanol, or a mixture thereof.

Moreover, draining may be carried out using a sieve having a fine mesh as long as the animal body tissue does not flow through, or draining may be carried out by means of centrifugal force. Furthermore, the drained animal body tissue is immersed in acetone, ethanol, etc. and recovered and the acetone, ethanol, etc. permeating the animal body tissue is evaporated, thus removing moisture in the animal body tissue as well as carrying out further delipidation.

Subsequently, an immersion treatment is carried out by placing the drained animal body tissue in a container, adding a salt solution (0.1 to 2 M, and preferably 0.8 to 1.2 M aqueous sodium chloride solution) at least 2 times by volume relative to the weight of the animal body tissue, and preferably 2 to 20 times by volume, and stirring at 2° C. to 10° C. for 12 to 48 hours, and preferably 20 to 30 hours (step S5). Such an immersion treatment allows unwanted protein other than collagen to be removed in advance.

When the amount of salt solution is less than 2 times by volume relative to the weight of the animal body tissue, the efficiency of extraction of unwanted protein is low, and when it exceeds 20 times by volume, it is difficult to handle; it is therefore preferable to carry out the immersion treatment with an amount of 2 to 20 times by volume relative to the weight of the animal body tissue. Furthermore, when the immersion treatment temperature is less than 2° C., there is a possibility of freezing, and when it exceeds 10° C., microbes grow. With regard to the time for one immersion treatment, extraction of unwanted protein is insufficient when it is 12 hours or less, and it is unnecessary for it to exceed 48 hours.

The salt solution used in the immersion treatment employs an aqueous solution of sodium chloride in FIG. 1, and it is desirable to employ a salt solution at 2° C. to 10° C. containing at least any one of sodium chloride, potassium chloride, calcium chloride, and barium chloride, the total amount of sodium chloride, potassium chloride, calcium chloride, and barium chloride added to this salt solution being 0.1 to 2 mol per L, and preferably 0.8 to 1.2 mol.

After an immersion treatment using, for example, 10 times by volume, relative to the weight of the animal body tissue, of a 1M aqueous solution of sodium chloride is carried out at 4° C. for 24 hours, the animal body tissue and the salt solution are separated, and the salt solution so separated is subjected to a quantitative analysis of total protein weight by, for example, a burette method (step S6). If the total protein weight contained in the salt solution exceeds 0.1 mg/mL, it is determined that unwanted protein that can be further removed is present in the animal body tissue, and the immersion treatment is repeated, but if the total protein weight contained in the salt solution is 0.1 mg/mL or less, it is determined that unwanted protein has been removed, and the operation moves to the subsequent step S7. Such an immersion treatment may or may not be carried out or may be carried out a plurality of times; in general, more unwanted protein can be removed when the number of repetitions is larger, and animal body tissue having a high insoluble elastin content can be obtained.

Subsequently, the animal body tissue that has undergone the immersion treatment is subjected to a collagen removal treatment by placing it in at least 2 times by volume, and preferably 2 to 20 times by volume, relative to the weight of the tissue, of an alkaline solution (0.05 to 0.5 M aqueous sodium hydroxide solution, preferably 0.05 to 0.3 M, and yet more preferably 0.05 to 0.15 M) and stirring it at 90° C. to 105° C., and preferably 95° C. to 100° C., for 10 to 20 minutes (step S7). If the amount of alkaline solution is less than 2 times by volume relative to the weight of the animal body tissue, the collagen extraction efficiency decreases, and if it exceeds 20 times by volume, handling becomes difficult; it is therefore desirable that the collagen removal treatment is carried out using the alkaline solution at 2 to 20 times by volume relative to the weight of the animal body tissue. If the time for the collagen removal treatment is less than 10 minutes, the collagen removal efficiency is poor, and if it exceeds 20 minutes, elastin undergoes decomposition; it is therefore desirable that the treatment is carried out for 10 to 20 minutes.

As the alkaline solution, in FIG. 1 an aqueous solution of sodium hydroxide is used, but the alkaline solution used may be an alkaline solution containing at least any one of sodium hydroxide, potassium hydroxide, calcium hydroxide, and barium hydroxide, and the total amount of sodium hydroxide, potassium hydroxide, calcium hydroxide, and barium hydroxide added to the alkaline solution is 0.05 to 0.5 mol per L, preferably 0.05 to 0.3 mol per L, and more preferably 0.05 to 0.15 mol per L.

After the collagen removal treatment is carried out using, for example, 10 times by volume, relative to the weight of the animal body tissue, of a 0.1M aqueous solution of sodium hydroxide at 100° C. for 15 minutes, the animal body tissue and the alkaline solution are separated, and the alkaline solution so separated is subjected to a quantitative analysis of total protein weight by, for example, the burette method (step S8). If the total protein mass contained in the alkaline solution exceeds, for example, 0.1 mg/mL, it is determined that collagen that can be further removed is present in the animal body tissue, and the collagen removal treatment is repeated, but if the total protein contained in the alkaline solution is 0.1 mg/mL or less, it is determined that the collagen has been removed, and the collagen removal treatment is completed to give a high purity insoluble elastin.

Subsequently, at least 2 times by volume, and preferably 2 to 20 times by volume, relative to the weight, of a solubilizing liquid is added to the insoluble elastin, and stirring is carried out at 90° C. to 105° C., and preferably 95° C. to 100° C., for 20 to 120 minutes, and preferably 40 to 80 minutes, so as to fragment the insoluble elastin and free and dissolve it in the solubilizing liquid as a water-soluble elastin (step S9). The solubilizing liquid used here is oxalic acid in FIG. 1, but it may be another acidic solution or an alkaline solution.

Examples of the acidic solution include an acidic solution containing at least any one of oxalic acid, formic acid, acetic acid, succinic acid, malic acid, tartaric acid, citric acid, benzoic acid, betaine, difluoroacetic acid, trifluoroacetic acid, phosphoric acid, sulfamic acid, perchloric acid, and trichloroacetic acid, the total amount of these acids being 0.1 to 0.5 mol per L, and preferably 0.2 to 0.3 mol per L.

Furthermore, examples of the alkaline solution that can be used include an alkaline solution containing at least any one of sodium hydroxide, potassium hydroxide, calcium hydroxide, and barium hydroxide, the total amount of sodium hydroxide, potassium hydroxide, calcium hydroxide, and barium hydroxide added to the alkaline solution being 0.05 to 0.5 mol per L, and preferably 0.05 to 0.3 mol per L.

After the animal body tissue is immersed in the solubilizing liquid, which is, for example, 10 times by volume, relative to the weight thereof, of a 0.25 M aqueous solution of oxalic acid, at 100° C. for 60 minutes, insoluble elastin and the solubilizing liquid are separated (step S10), and the separated solubilizing liquid is cooled to 25° C. or below by allowing it to cool, water-cooling, etc., and preferably to 10° C. or below by ice-cooling, etc. (step S11). That is, by cooling the separated solubilizing liquid to 25° C. or below, and preferably 10° C. or below by ice-cooling, etc., it is possible to suppress the reactivity of the solubilizing liquid and prevent the water-soluble elastin that has been freed and dissolved in the solubilizing liquid from being cut up. If insoluble elastin remains when the above separation is carried out, the insoluble elastin is immersed again in fresh solubilizing liquid to thus carry out solubilization of the insoluble elastin (step S12). This treatment with a solubilizing liquid is repeated until the insoluble elastin substantially completely dissolves.

Subsequently, the pH of the solubilizing liquid in which the water-soluble elastin has dissolved is adjusted to 5 to 7, and preferably 6 to 7, and the solubilizing liquid is subjected to dialysis (step S13). The solubilizing liquid in which the water-soluble elastin has been freed and dissolved is placed in a bag formed from a semipermeable membrane and sealed, and dialysis is then carried out against water under conditions of 4° C. to 10° C. so that components contained in the solubilizing liquid are leached outside the semipermeable membrane while leaving the water-soluble elastin within the bag, thus carrying out purification of the water-soluble elastin. When carrying out dialysis, the method is not limited to one employing a semipermeable membrane, and any method may be employed as long as, under conditions in which water-soluble elastin molecules can be recovered, other components in the solubilizing liquid and a salt formed when adjusting the pH can be removed. After 24 hours have elapsed, water used for the dialysis is discarded, dialysis is carried out again against fresh water at 4° C. to 10° C. for 24 hours, and this is preferably repeated at least 4 times.

The water-soluble elastin that has been dialyzed is subjected to phase separation by setting the temperature of the aqueous solution at 30° C. to 50° C. (step S14), and it is separated into an upper layer containing a low-molecular-weight water-solution elastin (equilibrium liquid phase) and a lower phase containing a high-molecular-weight water-soluble elastin (coacervate phase) (step S15). In particular, when the water-soluble elastin thus obtained is used as a tissue culture substrate for regenerative medicine, since tissue culturing is often carried out at about 37° C., it is desirable that a high-molecular-weight water-soluble elastin that undergoes coacervation at 37° C. or below is efficiently recovered. Since the coacervate phase is formed by elastin molecules themselves hydrophobically associating to form a molecular aggregate, the higher the molecular weight, the easier it is for aggregation into the coacervate phase to occur. Because of this, a high-molecular-weight water-soluble elastin can be efficiently recovered from the coacervate phase. Phase separation can be carried out if the elastin is in a water-soluble state, but a high-molecular-weight water-soluble elastin is efficiently obtained by carrying out the phase separation after adjusting the pH subsequent to dialysis so as to be preferably pH3 to pH7, and more preferably pH4 to pH6, which is in the vicinity of the isoelectric point of the water-soluble elastin.

The high-molecular-weight water-soluble elastin of the present invention is recovered from the coacervate phase, and the low-molecular-weight water-soluble elastin of the present invention is recovered from the upper layer (equilibrium liquid phase) separated therefrom.

A second process for producing the high-purity water-soluble elastin of the present invention is the process according to Embodiment 8. That is, it is a process for producing a water-soluble elastin from animal body tissue, the process comprising (1) a step of pretreating animal body tissue, (2) a step of carrying out alkali extraction by immersing the pretreated animal body tissue in an alkaline solution and removing a solution containing collagen and other unwanted protein extracted from the animal body tissue, (3) a step of carrying out alkali dissolution by dissolving the animal body tissue residue, after repeating the operation of (2) above, so as to recover a solution containing freed water-soluble elastin, and (4) a step of separating the solution containing the water-soluble elastin recovered in the alkali dissolution step into two layers by a phase separation operation, recovering a low-molecular-weight water-soluble elastin from the upper layer, and recovering a high-molecular-weight water-soluble elastin from the lower layer.

A method for pretreating animal body tissue, in relation to step (1) of the second process, involves a treatment for removing unwanted portions of the animal body tissue, a treatment for finely cutting the animal body tissue, or a treatment for delipidating the animal body tissue, and it is necessary to carry out at least one of these treatments (Embodiment 11).

In the alkali extraction step related to step (2) of the second process, it is preferable for the pretreated animal body tissue to be immersed in an alkaline solution containing, per L of solution, 0.05 to 0.5 mol of one or more alkali compounds selected from the group consisting of sodium hydroxide, potassium hydroxide, calcium hydroxide, and barium hydroxide, preferably 0.05 to 0.3 mol, and more preferably 0.05 to 0.15 mol, at 90° C. to 105° C., and preferably 95° C. to 100° C., for 10 to 20 minutes (Embodiment 9). The solution extracted from the animal body tissue is removed. Such a treatment allows collagen and other unwanted protein to be removed.

Subsequently, in the alkali dissolution step related to step (3) of the second process, after repeating the operation of step (2) above, remaining animal body tissue residue is dissolved and the solution is recovered. In step (3), the remaining animal body tissue residue is immersed and dissolved in an alkaline solution containing, per L of solution, 0.05 to 0.5 mol, and preferably 0.05 to 0.3 mol, of one or more alkali compounds selected from the group consisting of sodium hydroxide, potassium hydroxide, calcium hydroxide, and barium hydroxide (an alkaline solution having a higher concentration than that of step (2) above) at 90° C. to 105° C., and preferably 95° C. to 100° C., for 20 to 240 minutes, and preferably 40 to 120 minutes (a treatment time longer than the treatment time in step (2) above) (Embodiment 10). If animal body tissue residue remains, the animal body tissue residue is immersed again in a fresh alkaline solution, and this treatment with alkaline solution is repeated until the animal body tissue residue completely dissolves.

Since leaching of collagen and other unwanted protein by an alkaline solution under the above-mentioned conditions is carried out prior to fragmentation of insoluble elastin, in the alkali extraction step of (2) of the second process, the amount of unwanted protein, including collagen, that is leached decreases each time extraction from the animal body tissue is repeated, and solutions that are gradually diluted and in which the concentration of protein such as collagen exponentially decreases are obtained. Subsequently, in the alkali dissolution step of (3), by dissolving the remaining animal body tissue residue water-soluble elastin is freed and dissolves in the alkaline solution. In the methods of steps (2) and (3), by changing the concentration of the alkaline solution and the treatment time, operations from removal of unwanted protein including collagen to recovery of water-soluble elastin can be carried out intermittently and in sequence, and it is therefore possible to produce a water-soluble elastin in a short period of time.

Subsequently, in step (4) of the second process, the solution containing elastin recovered in the alkali dissolution step (3) is subjected to phase separation, and a low-molecular-weight water-soluble elastin is recovered from the upper layer thus separated. A high-molecular-weight water-soluble elastin is recovered from the lower layer thus separated. Such recovery steps may be carried out in the same manner as in the case of the first process.

Figure 2:
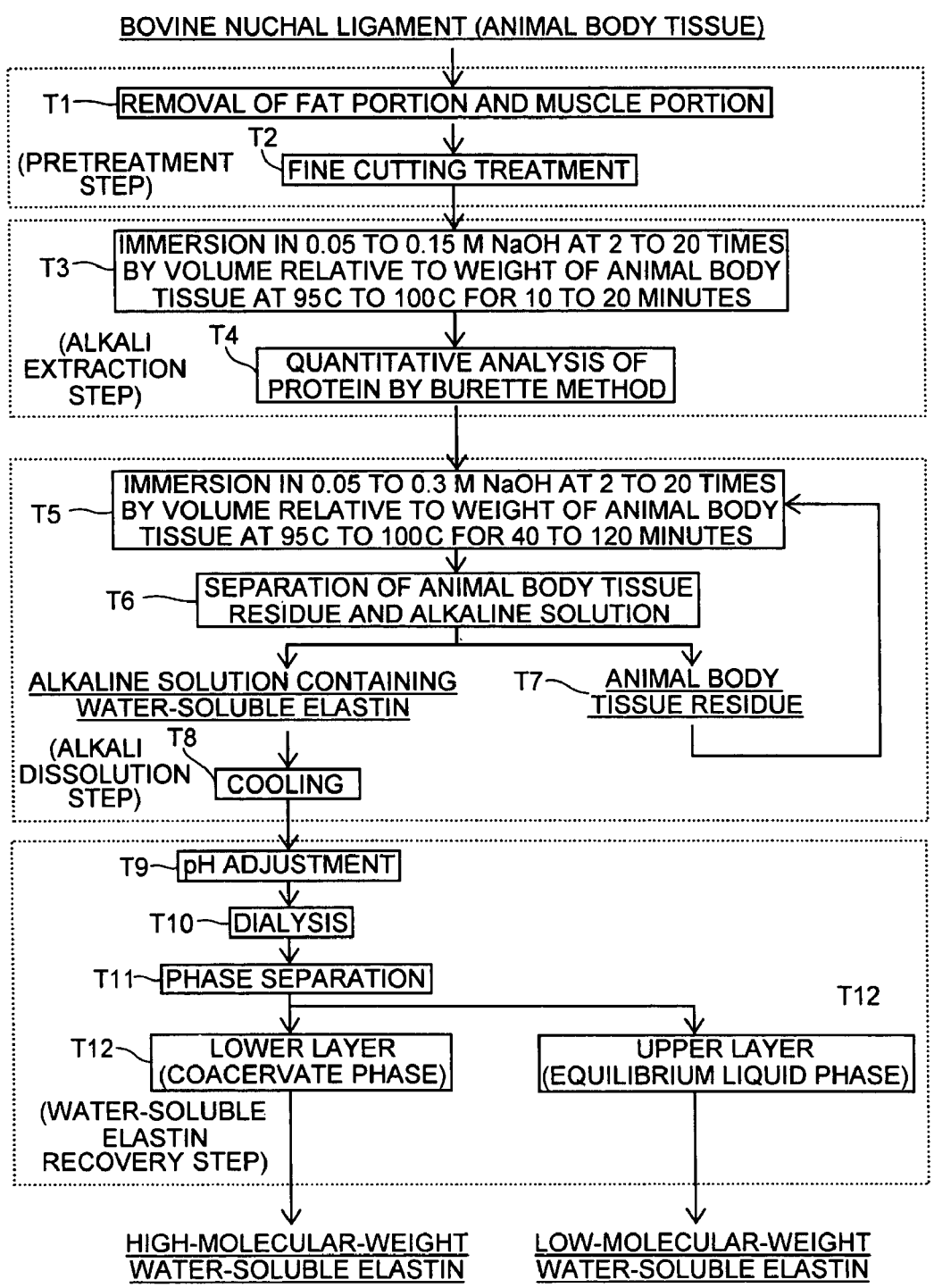

FIG. 2 shows a flow diagram when a water-soluble elastin is produced by the second process. The explanation below is given with reference to FIG. 2. In accordance with this process, a water-soluble elastin can be produced from animal body tissue in a short period of time. The treatment conditions, etc. in FIG. 2 are shown as one example of the present invention.

As a pretreatment step, a treatment for removing unwanted portions by scraping off portions having a low elastin content such as fat and muscle attached to bovine nuchal ligament, which is used as the animal body tissue, by means of a knife, etc. (step T1), and a treatment for finely cutting the animal body tissue by homogenizing it using a homogenizer in the same manner as in the first process (step T2) are carried out. Such pretreatment steps may be carried out in the same manner as in the first process.

Subsequently, an alkali extraction step is carried out by immersing the animal body tissue in at least 2 times by volume relative to the weight of the tissue, and preferably 2 to 20 times by volume, of an alkaline solution (0.05 to 0.5 M, preferably 0.05 to 0.3M, and more preferably 0.05 to 0.15 M aqueous solution of sodium hydroxide) and stirring it at 90° C. to 105° C., and preferably 95° C. to 100° C., for 10 to 20 minutes (step T3). Following this, the animal body tissue residue and the alkaline solution are separated, and the alkaline solution so separated is subjected to a quantitative analysis of total protein by, for example, the burette method (step T4). If the total amount of protein contained in the alkali solution exceeds, for example, 0.1 mg/mL, it is determined that collagen and other unwanted protein that can be further removed are present in the animal body tissue, and the removal treatment for collagen, etc. is repeated, but if the total amount of protein contained in the alkaline solution is 0.1 mg/mL or less, it is determined that collagen and other unwanted protein have been removed, and the removal treatment for collagen, etc. is completed.

If the amount of alkaline solution is less than 2 times by volume relative to the weight of the animal body tissue, the efficiency of extracting collagen or unwanted protein deteriorates, but if it exceeds 20 times by volume, it is difficult to handle, and it is preferable for it to be 2 to 20 times by volume relative to the weight of the animal body tissue. If the immersion time is less than 10 minutes, the efficiency of removing collagen or other unwanted protein is poor, but if it exceeds 20 minutes, even elastin suffers from decomposition and is extracted, and it is therefore preferable for the immersion time to be 10 to 20 minutes.

As the alkaline solution, an aqueous solution of sodium hydroxide is used in FIG. 2, but another alkaline solution may be used. In particular, it is desirable to use an alkaline solution containing a total of 0.05 to 0.5 mol per L of one or more of sodium hydroxide, potassium hydroxide, calcium hydroxide, and barium hydroxide, preferably 0.05 to 0.3 mol per L, and more preferably 0.05 to 0.15 mol per L. The alkali extraction step has an effect in delipidating the animal body tissue. Therefore, in FIG. 2, a delipidation step is omitted in the pretreatment step, but as in FIG. 1 a delipidation operation may be carried out so as to further remove unwanted lipid.

The animal body tissue residue that has undergone the alkali extraction step is subsequently immersed in at least 2 times by volume, relative to the weight of the tissue, and preferably 2 to 20 times by volume, of an alkaline solution (a 0.05 to 0.5 M, and preferably 0.05 to 0.3 M aqueous solution of sodium hydroxide) and stirred at 90° C. to 105° C., and preferably 95° C. to 100° C., for 20 to 240 minutes, and preferably 40 to 120 minutes so as to dissolve the animal body tissue residue, thus freeing water-soluble elastin (step T5). As the alkaline solution, an aqueous solution of sodium hydroxide is used in FIG. 2, but another alkaline solution may be used. In particular, it is desirable to use an alkaline solution containing a total of 0.05 to 0.5 mol per L of one or more of sodium hydroxide, potassium hydroxide, calcium hydroxide, and barium hydroxide, and preferably 0.05 to 0.3 mol per L. When animal body tissue residue is present, an operation of separating the alkaline solution containing water-soluble elastin from undissolved animal body tissue residue is carried out (step T6), and the remaining animal body tissue residue is subjected again to an alkali dissolution step (step T7).

Subsequently, since the majority of the protein contained in the alkaline solution thus separated is water-soluble elastin, the temperature is decreased to 25° C. or below by allowing it to cool, water-cooling, etc., and preferably to 10° C. or below by ice-cooling, etc. (step T8), the pH is adjusted so as to be around neutral (step T9), and dialysis is carried out (step T10). The means and methods for dialysis may be the same as in the case of the first process.

Thereafter, in the same manner as in the case of the first process, the liquid preparation thus dialyzed is subjected to phase separation by setting the temperature of the aqueous solution at 30° C. to 50° C. (step T11), thus separating it into an upper layer containing a low-molecular-weight water-solution elastin (equilibrium liquid phase) and a lower layer containing a high-molecular-weight water-soluble elastin (coacervate phase) (step T12). Recovery steps for such a low-molecular-weight aqueous-solution elastin and high-molecular-weight water-soluble elastin may be carried out in the same manner as in the case of the first process.

In the present invention, for example, the content of protein in the alkaline solution after the collagen removal treatment may be measured after each of the collagen removal treatments by a quantitative protein method such as the burette method, thus determining the point of completion of the operation. In the burette method, since unwanted protein, collagen, etc. that has leached into the alkali solution exhibits a reddish purple color, it is quantitatively analyzed by measuring at, for example, a wavelength around 540 nm, preferably using a spectrophotometer, and the point at which the concentration of protein in the solution becomes a predetermined value or less may be defined as the point of completion. Alternatively, the point of completion of the immersion treatment may be determined in a simple way by carrying out the treatment until a reddish purple color cannot be seen by eye.

The predetermined value here may be determined according to a desired purity for the water-soluble elastin. When, for example, 10 times by volume, relative to the weight of the animal body tissue, of the alkaline solution is added, a predetermined value for obtaining a relatively high-purity water-soluble elastin may be, for example, 0.1 mg/mL, and a predetermined value for obtaining a higher purity water-soluble elastin may be, for example, 0.1 mg/mL or less. 'Completion when it becomes a predetermined value or less' referred to in the present invention includes a case in which a treatment is further repeated after it becomes a predetermined value or less and then the treatment is completed.

Regardless of whether the solubilizing liquid is either acidic or alkaline, it is also possible to prevent the water-soluble elastin that has dissolved in the solubilizing liquid from being cut up by intermittently repeating solubilization of insoluble elastin until the insoluble elastin dissolves and disappears. That is, after immersion in the solubilizing liquid is carried out for 20 to 120 minutes, and preferably 40 to 80 minutes, the solubilization is temporarily interrupted, the solubilizing liquid obtained by separation from the insoluble elastin is cooled to 25° C. or below by allowing it to stand, water-cooling, etc., and preferably to 10° C. or below by ice-cooling, etc. without exposing it continuously to high temperature conditions at 90° C. to 105° C., and preferably 95° C. to 100° C., and the reactivity of the solubilizing liquid can thereby be reduced, thus making it possible to prevent the water-soluble elastin from being cut up.

The water-soluble elastin that has dissolved in the solubilizing liquid may be subjected to a phase separation operation and fractionated into two layers, that is, an upper layer (equilibrium liquid phase), which is a low-molecular-weight water-soluble elastin fraction, and a lower layer (coacervate phase), which is a high-molecular-weight water-soluble elastin fraction. Since only high-molecular-weight water-soluble elastin molecules associate hydrophobically into a molecular aggregate to thus form a coacervate phase, by obtaining a coacervate phase, a high-molecular-weight water-soluble elastin can be recovered efficiently. Furthermore, when carrying out the phase separation, by adjusting the pH of the water-soluble elastin so as to be 3 to 7, and preferably 4 to 6, it becomes close to the isoelectric point of elastin, thus making it easy to form a coacervate phase, and the amount of high-molecular-weight water-soluble elastin recovered can be increased.

The first process has the merit that, since insoluble elastin is actually taken out of the reaction system, the amino acid composition, etc. of the insoluble elastin taken out can be analyzed and the purity thereof ascertained. Furthermore, it has the merit that insoluble elastin is stable and can be stored for a long period of time, and the solubilization method may be selected freely from an acid treatment and an alkali treatment. On the other hand, in the second process, since insoluble elastin is not taken out, the process is simple, and merely by adjusting the concentration of the alkaline solution and the reaction time, a high-purity water-soluble elastin can be obtained. Because of this, the latter process gives a water-soluble elastin in high yield.

As hereinbefore described, the water-soluble elastin obtained by the first or second process is subsequently subjected to phase separation to give low-molecular-weight (molecular weight about 10,000 to 30,000) water-soluble elastin and high-molecular-weight (molecular weight about 30,000 to 300,000) water-soluble elastin fractions. That is, when the water-soluble elastin is heated to 30° C. to 50° C., it undergoes phase separation and becomes cloudy, and by allowing it to stand as it is, it separates into two layers. A low-molecular-weight water-soluble elastin is recovered from the upper layer fraction, which is an equilibrium liquid phase, and a high-molecular-weight water-soluble elastin is recovered from the lower layer fraction, which is a coacervate phase. From the results of measurement of the molecular weight thereof and the results of measurement of the amino acid composition, the low-molecular-weight water-soluble elastin and the high-molecular-weight water-soluble elastin of the present invention can both be evaluated as having high purity.

Furthermore, as a result of examination of the coacervation properties of the low-molecular-weight water-soluble elastin and the high-molecular-weight water-soluble elastin, that is, the reversible properties such that the turbidity is increased by increasing the temperature and the turbidity is returned to its original level by decreasing the temperature, it is confirmed that the high-molecular-weight water-soluble elastin becomes cloudy when heated, and it can be expected that, since the turbidity curve is reversible, the high-molecularweight water-soluble elastin will find application in cosmetics or medical materials. On the other hand, since the low-molecular-weight water-soluble elastin does not become cloudy when heated, it is difficult to apply it to cosmetics or medical materials. However, since the low-molecular-weight water-soluble elastin has a low molecular weight, it is advantageous in terms of digestive absorption, and it can be expected that it will be suitable for a food material or a medicine.

A solution of collagen becomes cloudy when heated, but even by reducing the temperature the cloudiness remains and the original transparent state cannot be obtained (nonreversible). In contrast thereto, a solution of water-soluble elastin becomes cloudy when heated, and by reducing the temperature the original transparent state is obtained (reversible). Furthermore, when the heating temperature is extremely high, collagen is denatured and turned into gelatin, which has different properties from those of collagen, whereas elastin remains unchanged even when the heating temperature is extremely high. Utilizing such properties, collagen and elastin can be respectively applied to appropriate medical materials. Moreover, it is possible to ascertain the presence or absence of collagen contamination by examining whether or not the turbidity curve of a water-soluble elastin produced is reversible.

Among the water-soluble elastins of the present invention, since a low-molecular-weight water-soluble elastin having a molecular weight of about 10,000 to 30,000 in which 79% to 84% of the constituent amino acids of the elastin comprises proline, glycine, alanine, and valine, 2% to 3% comprises aspartic acid and glutamic acid, 0.7% to 1.3% comprises lysine, histidine, and arginine, and 0.2% to 0.4% comprises desmosine and isodesmosine has excellent digestive absorption, it can be used as a functional food. At present, the health food market is growing rapidly, and although there are functional foods individually targeted at symptoms such as high cholesterol, high triglycerides, and high blood pressure, there is no universal functional food that can generally prevent and inhibit arteriosclerosis. The main component forming blood vessels is elastin (about 30%), and the next is collagen (about 18%); although collagen is widely used as a food material having a skin beauty effect, an arteriosclerosis preventing/inhibiting functional food employing elastin as a material has not yet been developed.

Japan Food Industry Center Technical Research Report, No. 27, 2001, pp. 21-26 reports that when a water-soluble elastin (molecular weight unknown) produced by a treatment with an enzyme having elastase activity was administered to a high-fat diet rat and a healthy subject, the total cholesterol, triglycerides, etc. in blood decreased, and lipid metabolism abnormalities in blood were improved. However, not only was the water-soluble elastin used in this report considerably different (proline, glycine, alanine, and valine comprising only 68%) in terms of amino acid composition from water-soluble elastins that up until now have been evaluated to have high purity, but it can also be assumed that, since neither desmosine nor isodesmosine, which are amino acids characteristic of elastin, were detected, it had extremely low purity or was different from elastin.

Since it has been proved as hereinafter described that the low-molecular-weight water-soluble elastin of the present invention has an effect in improving lipid metabolism abnormalities in blood, such as suppressing an increase in cholesterol, suppressing an increase in triglycerides, suppressing an increase in LDL-cholesterol (bad cholesterol), suppressing a decrease in HDL-cholesterol (good cholesterol), and suppressing an increase in lipid peroxide, an effect in suppressing sclerotic lesions of the surface of the intravascular lumen, and an effect in suppressing a decrease in vascular elastic function, it can be expected that it will be developed as a universal functional food for arteriosclerosis prevention/inhibition.

Furthermore, as hereinbefore described, the low-molecular-weight water-soluble elastin of the present invention has physiological functions such as an effect in improving lipid metabolism abnormalities in blood, such as suppressing an increase in cholesterol, suppressing an increase in triglycerides, suppressing an increase in LDL-cholesterol (bad cholesterol), suppressing a decrease in HDL-cholesterol (good cholesterol), suppressing an increase in lipid peroxide, and suppressing an increase in oxidized LDL, an effect in suppressing thrombogenesis, an effect in suppressing sclerotic lesions of the surface of the intravascular lumen (hard plaque), and an effect in suppressing a decrease in vascular elastic function. It can therefore be expected that the low-molecular-weight water-soluble elastin of the present invention will be developed as an active ingredient in various types of therapeutic or preventive medicines such as, for example, an antiarteriosclerotic agent, a lipidosis improving agent, and an antithrombogenic agent.

When the low-molecular-weight water-soluble elastin of the present invention is used as a food or a medicine, it may be used as an active ingredient, and a metal useful to the living body such as, for example, an alkaline earth metal or a transition metal such as magnesium, calcium, chromium, manganese, iron, cobalt, nickel, copper, aluminum, or zinc may be used in combination. A synergistic effect can be obtained depending on the metal used.

In the present invention, the configuration of the functional food is not particularly limited; a low-molecular-weight water-soluble elastin having a molecular weight of about 10,000 to 30,000 may be prepared as a drink or a food as it is, it may be mixed with various types of protein, saccharide, fat, trace element, vitamin, etc., it may be made into a liquid, a semiliquid, or a solid, or it may be added to a general drink or food. The food referred to here is used in a wide sense to mean a health food, a health supplement, a food for a specific health use, etc. Since the functional food of the present invention can be expected to exhibit an effect in improving lipid metabolism abnormalities in blood, an effect in suppressing sclerotic lesions of the surface of the intravascular lumen, and an effect in suppressing a decrease in vascular elastic function, it can be provided as a universal functional food for arteriosclerosis prevention/inhibition.

In the present invention, a medicine may be produced by mixing a low-molecular-weight water-soluble elastin having a molecular weight of about 10,000 to 30,000 as an active ingredient with a pharmaceutically acceptable additive. The medicine of the present invention may be administered orally or parenterally. Examples of the oral agent include a granular agent, a powdered agent, a tablet, a pill, a capsule, a syrup, an emulsion, and a suspension. Examples of the parenteral agent include injection and drops. These preparations may be prepared by standard means and methods that are normally carried out in the drug preparation field using a pharmaceutically acceptable carrier.

The intake of the functional food of the present invention per adult per day is desirably 30 to 6,000 mg on an elastin basis, and preferably 60 to 3,000 mg. When administered as a medicine, the amount depends on the age, weight, and symptoms of the subject, the administration time, the form of the agent, the administration method, combination with drugs, etc, and when the active ingredient of the present invention is orally administered as a medicine, the amount per adult is 0.5 to 100 mg/kg weight, and preferably 1 to 50 mg/kg weight.

EXAMPLE 1

Production of Water-Soluble Elastin

Bovine nuchal ligament was used as animal body tissue, portions having a low elastin content such as attached fat or muscle were scraped off using a knife, etc., and the animal body tissue was homogenized using a homogenizer. The animal body tissue thus homogenized was boiled in boiling water for 1 hour in order to delipidize it, and then drained. This delipidation step may be carried out a plurality of times, and in order to improve the delipidation efficiency, a treatment with a dilute alkaline solution or an organic solvent may be carried out.

The homogenized and delipidized animal body tissue was placed in a container, 10 times by volume relative to the weight of the animal body tissue (10 mL per g weight) of a 1 M aqueous solution of sodium chloride was added thereto so that the animal body tissue was immersed, and stirring was carried out at 4° C. for 24 hours. The animal body tissue and the salt solution were separated, the salt solution thus separated was subjected to a quantitative analysis of total protein by the burette method, and if the total amount of protein contained in the salt solution was 0.1 mg/mL or less, it was judged that unwanted protein had been removed. If unwanted protein had not been removed, this operation could be carried out a plurality of times. This immersion treatment for removing unwanted protein is not essential, but may be carried out a plurality of times if necessary.

The animal body tissue after the immersion treatment was placed in 10 times by volume of a 0.1 M aqueous solution of sodium hydroxide, stirring was carried out at 100° C. for 15 minutes, and a collagen removal treatment was thus carried out. Subsequently, the animal body tissue and the alkaline solution were separated to give a pure insoluble elastin. The alkaline solution thus separated was subjected to a quantitative analysis of total protein by, for example, the burette method, if the total amount of protein contained in the alkaline solution was 0.1 mg/mL less, it was judged that collagen had been removed. If collagen had not been removed, this operation could be carried out a plurality of times.

Subsequently, 10 times by volume, relative to the weight of the insoluble elastin, of 0.25 M oxalic acid (solubilizing liquid) was added thereto, stirring was carried out at 100° C. for 60 minutes so as to fragment the insoluble elastin, and a water-soluble elastin was thus freed and dissolved in the solubilizing liquid. Following this, the insoluble elastin and the solubilizing liquid were separated, and the solubilizing liquid thus separated was cooled to 25° C. or below. Such an operation enabled the reactivity of the solubilizing liquid to be reduced, thus preventing the water-soluble elastin freed and dissolved in the solubilizing liquid from being cut up. When insoluble elastin remained, by repeating this operation the insoluble elastin could be solubilized.

Production of High-Molecular-Weight Elastin and Low-Molecular-Weight Elastin

Subsequently, the pH of the solubilizing liquid in which the water-soluble elastin was dissolved was adjusted so as to be 6 to 7, dialysis against water at 4° C. to 10° C. was carried out for at least 96 hours (changing water outside the dialysis membrane every 24 hours), thus carrying out purification of the water-soluble elastin. Subsequently, the water-soluble elastin thus dialyzed was subjected to phase separation by setting the temperature of the aqueous solution at 30° C. to 50° C., thus separating it into two layers. A low-molecular-weight (molecular weight about 10,000 to 30,000) water-soluble elastin was recovered from an upper layer fraction, and a high-molecular-weight (molecular weight about 30,000 to 300,000) water-soluble elastin was recovered from a lower layer fraction. Setting the temperature of the aqueous solution at 30° C. to 40° C. enabled the efficiency of recovery of the low-molecular-weight water-soluble elastin to be increased, and setting the temperature of the aqueous solution at 40° C. to 50° C. enabled the efficiency of recovery of the high-molecular-weight water-soluble elastin to be increased. Adjusting the pH so as to be 3 to 7, which is close to the isoelectric point of the water-soluble elastin, and preferably 4 to 6, enabled the efficiency of recovery of the high-molecular-weight water-soluble elastin to be increased. Such a phase separation operation allowed 20% to 50%, on a water-soluble elastin basis, of the low-molecular-weight fraction and 10% to 30% of the high-molecular-weight fraction to be recovered. The yield of the low-molecular-weight water-soluble elastin was 2% to 4% on a bovine nuchal ligament basis, and the yield of the high-molecular-weight water-soluble elastin was 1% to 2%.

The upper layer fraction and the lower layer fraction after the phase separation were subjected to SDS (sodium dodecylsulfate)-PAGE (polyacrylamide gel electrophoresis) under non-reducing conditions, the gel after the electrophoresis was stained, and it was confirmed from a stained band that the upper layer fraction was a low-molecular-weight water-soluble elastin having a molecular weight of about 10,000 to 30,000, and the lower layer fraction was a high-molecular-weight water-soluble elastin having a molecular weight of about 30,000 to 300,000.

The amino acid compositions of the low-molecular-weight water-soluble elastin and the high-molecular-weight water-soluble elastin were as shown in Table 1. The amino acid composition in Table 1 is expressed as an amino acid composition when the total number of amino acids is 1,000. The 'low molecular weight' referred to here means a low-molecular-weight water-soluble elastin having a molecular weight of about 10,000 to 30,000, and the 'high molecular weight' referred to here means a high-molecular-weight water-soluble elastin having a molecular weight of about 30,000 to 300,000. The content of histidine was on the order of 0.4 to 0.5 per 1,000 amino acid residues in the present invention, but it is shown as 0 in Table 1 due to rounding.

TABLE 1

| Amino acid | Low molecular | | High molecular | |
| --- | --- | --- | --- | --- |
| Asp + Asn | 7 | | 7 | |
| Thr | 9 | | 10 | |
| Ser | 11 | | 9 | |
| Glu + Gln | 17 | | 16 | |
| Pro | 116 | | 119 | |
| Gly | 321 | 812 | 323 | 814 |
| Ala | 230 | | 235 | |
| Val | 145 | | 137 | |
| Hyl | 0 | | 0 | |
| Ile | 24 | | 27 | |
| Leu | 58 | | 56 | |
| Tyr | 9 | | 7 | |
| Des + Ide | 3 | | 3 | |
| Phe | 31 | | 33 | |
| Lys | 5 | | 7 | |
| His | 0 | | 0 | |
| Arg | 7 | | 6 | |
| Hyp | 7 | | 5 | |

EXAMPLE 2

Production of Water-Soluble Elastin

As a pretreatment step, bovine nuchal ligament was used as animal body tissue, a treatment for removing unwanted protein was carried out by scraping off portions having low elastin content such as attached fat or muscle using a knife, etc., and subsequently a fine cutting treatment was carried out by homogenizing the animal body tissue using a homogenizer. The animal body tissue thus homogenized was boiled in boiling water for 1 hour in order to delipidize it, and then drained. This delipidation step may be carried out a plurality of times if the delipidation is not sufficient, and in order to improve the delipidation efficiency, a treatment with a dilute alkaline solution or an organic solvent may be carried out. In a case where fat is removed together with collagen or unwanted protein in the subsequent alkali extraction step, the delipidation treatment may be omitted here.

10 times by volume (10 mL per g weight), relative to the weight of the homogenized and delipidized animal body tissue, of a 0.1 M aqueous solution of sodium hydroxide was added thereto, and stirring was carried out at 100° C. for 15 minutes, thus carrying out a step of extracting and removing collagen and unwanted protein other than elastin (alkali extraction step). The animal body tissue residue and the alkaline solution were then separated. The alkaline solution thus separated was subjected to a quantitative analysis of total protein by, for example, the burette method, and if the total amount of protein contained in the alkaline solution was 0.1 mg/mL or less, it was judged that collagen and unwanted protein had been removed. If collagen and unwanted protein are not removed, this operation may be carried out a plurality of times.

Subsequently, the animal body tissue residue obtained above was added to 10 times by volume, relative to the weight of the tissue, of a 0.1 M aqueous solution of sodium hydroxide (solubilizing liquid), and an alkali dissolution step was carried out at 100° C. for 60 minutes. Following this, the animal body tissue residue and the alkaline solution were separated, and the separated alkaline solution containing water-soluble elastin was cooled to 25° C. or below. In this process, when the animal body tissue remains, this alkali dissolution step may be carried out a plurality of times.

Production of High-Molecular-Weight Elastin and Low-Molecular-Weight Elastin Subsequently, the pH of the alkaline solution containing the water-soluble elastin was adjusted so as to be around neutral, that is, 6 to 7, and dialysis against water was carried out at 4° C. to 10° C. for at least 96 hours (changing the water outside the dialysis membrane every 24 hours). Subsequently, the liquid obtained by dialysis was subjected to phase separation by setting the temperature of the aqueous solution at 30° C. to 50° C., thus separating it into two layers. A low-molecular-weight (molecular weight about 10,000 to 30,000) water-soluble elastin was recovered from the upper layer fraction, and a high-molecular-weight (molecular weight about 30,000 to 300,000) water-soluble elastin was recovered from the lower layer fraction (water soluble elastin recovery step). Setting the temperature of the aqueous solution at 30° C. to 40° C. enabled the efficiency of recovery of the low-molecular-weight water-soluble elastin to be increased, and setting the temperature of the aqueous solution at 40° C. to 50° C. enabled the efficiency of recovery of the high-molecular-weight water-soluble elastin to be increased. Adjusting the pH so as to be 3 to 7, which is close to the isoelectric point of the water-soluble elastin, and preferably 4 to 6, enabled the efficiency of recovery of the high-molecular-weight water-soluble elastin to be increased. Such a phase separation operation allowed 50% to 70%, on a water-soluble elastin basis, of the low-molecular-weight fraction and 20% to 30% of the high-molecular-weight to be recovered. The yield of the low-molecular-weight water-soluble elastin was 4% to 12% on a bovine nuchal ligament basis, and the yield of the high-molecular-weight water-soluble elastin was 2% to 5%. When the water-soluble elastin thus obtained is used as a tissue culture substrate for regenerative medicine, since tissue culturing is often carried out at about 37° C., it is desirable to efficiently recover a high-molecular-weight water-soluble elastin, which undergoes coacervation at 37° C. or below.

The upper layer fraction and the lower layer fraction after the phase separation were subjected to SDS (sodium dodecylsulfate)-PAGE (polyacrylamide gel electrophoresis) under non-reducing conditions, the gel after the electrophoresis was stained, and it was confirmed from a stained band that the upper layer fraction was a low-molecular-weight water-soluble elastin having a molecular weight of about 10,000 to 30,000, and the lower layer fraction was a high-molecular-weight water-soluble elastin having a molecular weight of about 30,000 to 300,000.

The amino acid compositions of the low-molecular-weight water-soluble elastin and the high-molecular-weight water-soluble elastin were as shown in Table 2. The amino acid composition in Table 2 is expressed as an amino acid composition when the total number of amino acids is 1,000. The 'low molecular weight' referred to here means a low-molecular-weight water-soluble elastin having a molecular weight of about 10,000 to 30,000, and the 'high molecular weight' referred to here means a high-molecular-weight water-soluble elastin having a molecular weight of about 30,000 to 300,000. The content of histidine was on the order of 0.4 to 0.5 per 1,000 amino acid residues in the present invention, but it is shown as 0 in Table 2 due to rounding.

TABLE 2

| Amino acid | Low molecular | | High molecular | |
| --- | --- | --- | --- | --- |
| Asp + Asn | 8 | | 6 | |
| Thr | 4 | | 5 | |
| Ser | 5 | | 6 | |
| Glu + Gln | 18 | | 17 | |
| Pro | 121 | | 119 | |
| Gly | 329 | 818 | 325 | 823 |
| Ala | 229 | | 233 | |
| Val | 140 | | 146 | |
| Hyl | 0 | | 0 | |
| Ile | 24 | | 25 | |
| Leu | 54 | | 57 | |
| Tyr | 9 | | 8 | |
| Des + Ide | 3 | | 3 | |
| Phe | 32 | | 30 | |
| Lys | 7 | | 5 | |
| His | 0 | | 0 | |
| Arg | 6 | | 5 | |
| Hyp | 11 | | 10 | |

COMPARATIVE EXAMPLE

A water-soluble elastin was produced in accordance with a method described in a production example of JP-A-60-258107. That is, bovine nuchal ligament was subjected to a sodium chloride treatment, a trichloroacetic acid treatment, and then a treatment with hot water at 120° C., thus giving a purified elastin. This was added to a solution of lactic acid, autoclaved, cooled, and then decomposed by the protease pepsin to give a water-soluble elastin having an average molecular weight of about 50,000.

The amino acid composition of the water-soluble elastin thus obtained was proline, glycine, alanine, and valine 77% in total, aspartic acid and glutamic acid 3.4% in total, and lysine, histidine, and arginine 1.5% in total, which are all different from the composition of the water-soluble elastin of the present invention. In particular, hydroxyproline was 15%, which is very large compared with the 7% of Examples 1 and 2 of the present invention, suggesting that the water-soluble elastin of Comparative Example was contaminated with collagen.

When the turbidity of the water-soluble elastin obtained in the Comparative Example was measured (coacervation), the temperature at which the turbidity started was higher than that in Examples 1 and 2 by about 10° C. This suggests that the elastin obtained in the Comparative Example had a low molecular weight and a low purity. The yield of the water-soluble elastin in the Comparative Example was only 3%, compared with the 11% of that obtained in Example 2 on a delipidized tissue basis.

EXAMPLE 3

In the present Example, the physiological function of the low-molecular-weight water-soluble elastins obtained in Examples 1 and 2 is explained.

Effect in Improving Lipid Metabolism Abnormalities in Blood

An arteriosclerosis model rabbit was experimentally prepared by loading with 0.5% cholesterol, a low-molecular-weight water-soluble elastin was orally administered thereto, and an effect in suppressing arteriosclerosis and an effect in improving lipid metabolism abnormalities in blood were examined. 12 male New Zealand White rabbits (weight about 2 kg) were divided into 3 groups of 4, that is, a control group, a cholesterol group, and a combined cholesterol group+elastin group, the control group was fed with 90 g/day of an ordinary diet (ORC4, manufactured by Oriental Yeast Co., Ltd.), the cholesterol group was fed with 90 g/day of a cholesterol diet (ORC4+0.5% cholesterol), and the combined cholesterol group+elastin group was fed with 90 g/day of a combined cholesterol+elastin diet (ORC4+0.5% cholesterol+0.1% to 0.5% elastin). After a predetermined period, blood was sampled and various types of examination were carried out. As elastin, the low-molecular-weight water-soluble elastin of the present invention was used.

Figure 3:
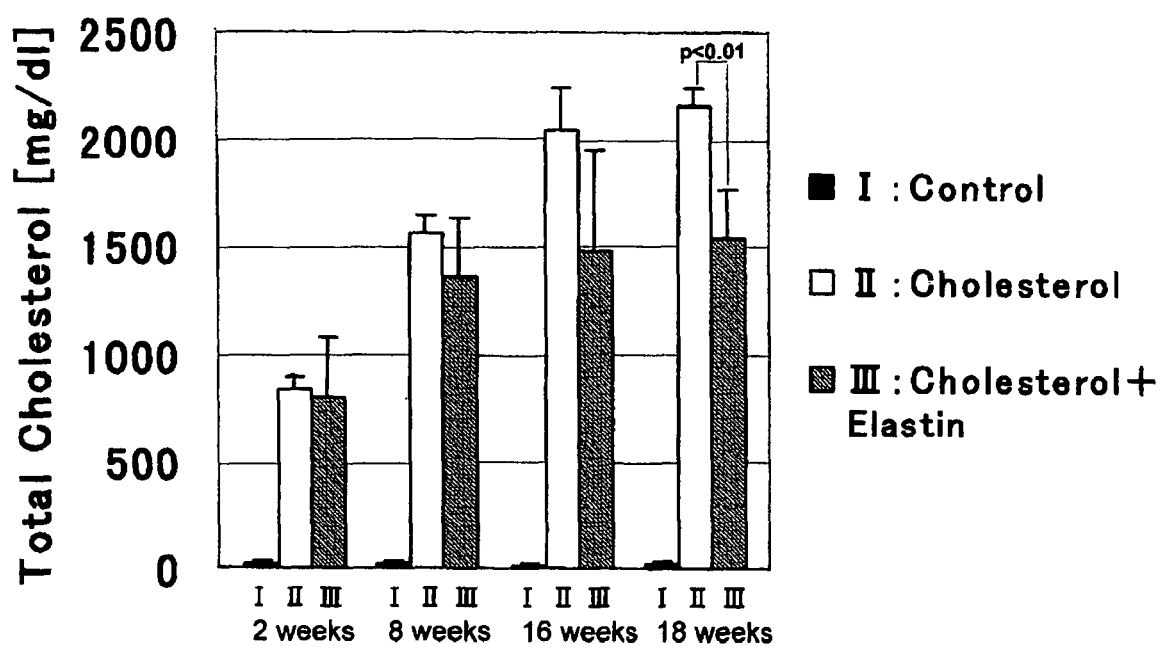
Figure 4:
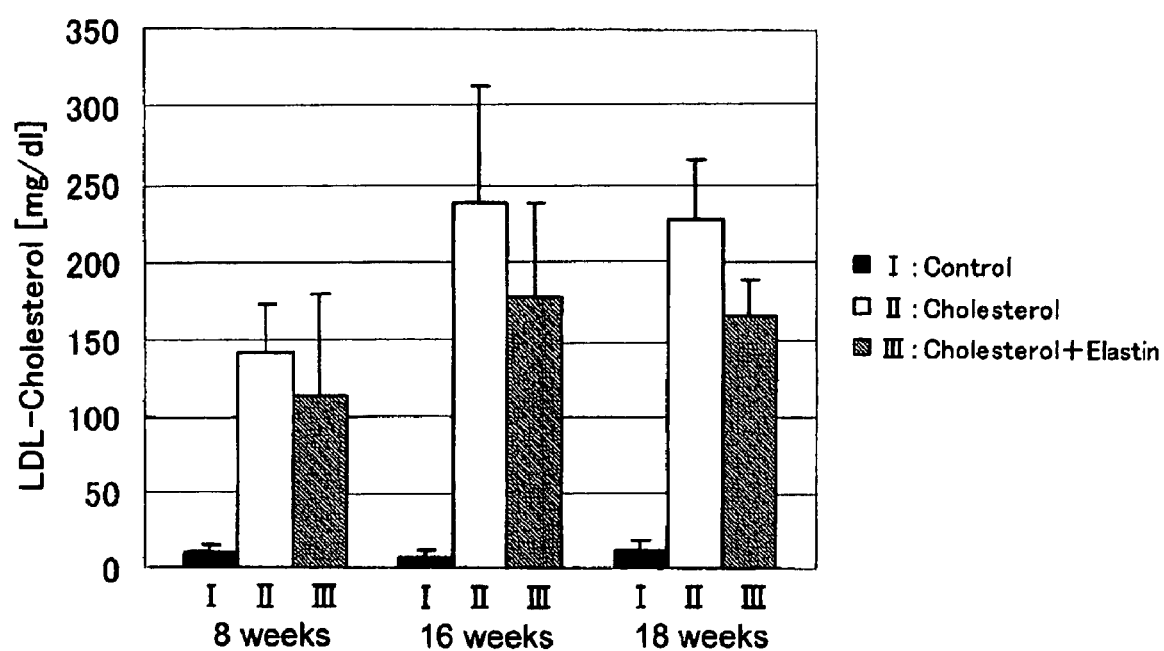
Figure 5:
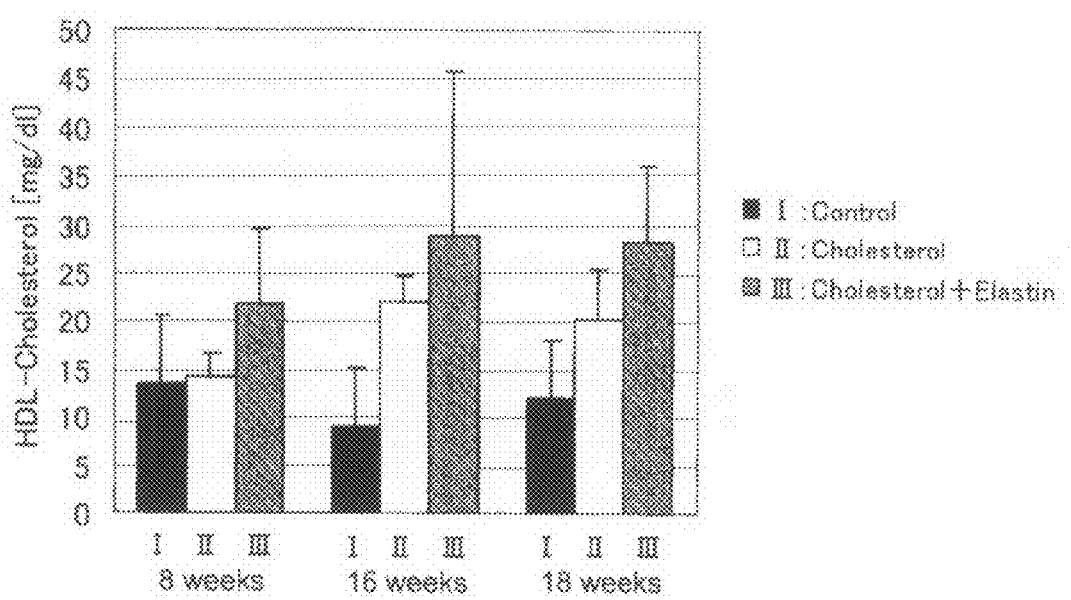
Figure 6:
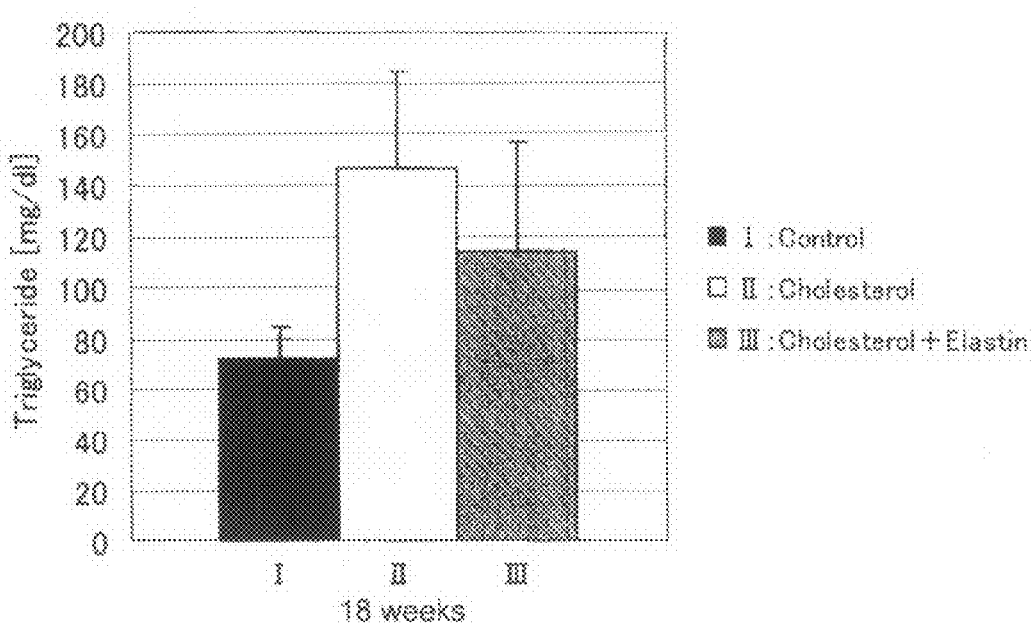
Figure 7:
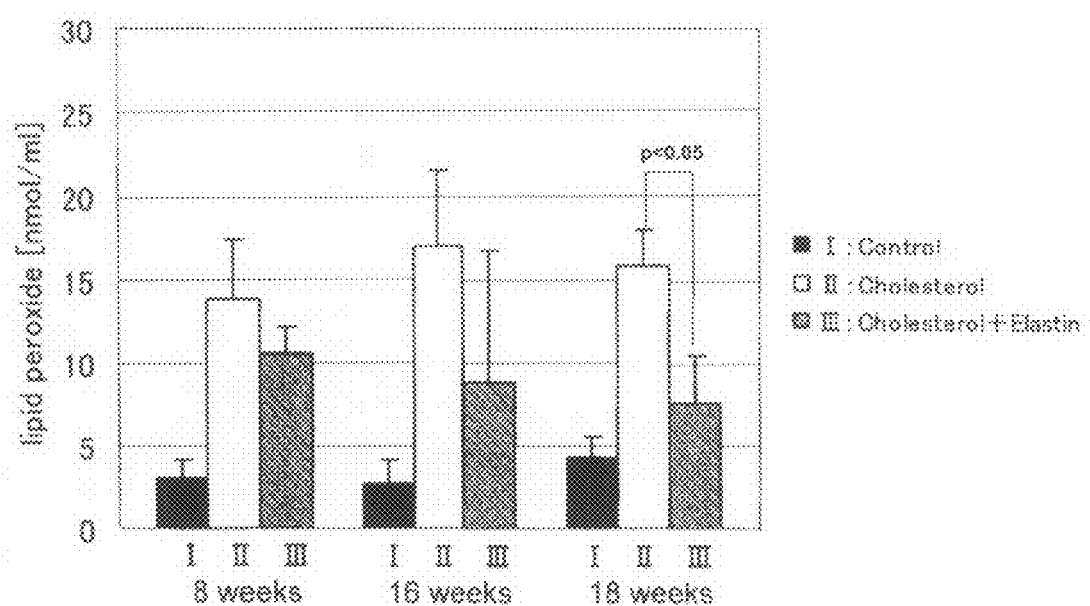

FIG. 3 shows change in total cholesterol in serum, FIG. 4 shows change in LDL-cholesterol, FIG. 5 shows change in HDL-cholesterol, FIG. 6 shows change in triglyceride, and FIG. 7 shows change in lipid peroxide. From these results, the lipid metabolism abnormalities in blood observed for the cholesterol group was improved for the combined cholesterol group+elastin group. That is, the low-molecular-weight water-soluble elastin of the present invention had an effect in decreasing total blood cholesterol; looked at in detail, it decreased the so-called bad LDL-cholesterol but increased the so-called good HDL-cholesterol. Furthermore, it also had effects in decreasing triglyceride and lipid peroxide.

These results indicate that the low-molecular-weight water-soluble elastin of the present invention has potential as a functional food material for improving lipid metabolism abnormalities in blood and consequently suppressing arteriosclerosis, and as a medicine for improving lipid metabolism abnormalities in blood and consequently suppressing arteriosclerosis.

Improving Arteriosclerosis or Degraded Vascular Elastic Function

Figure 8:
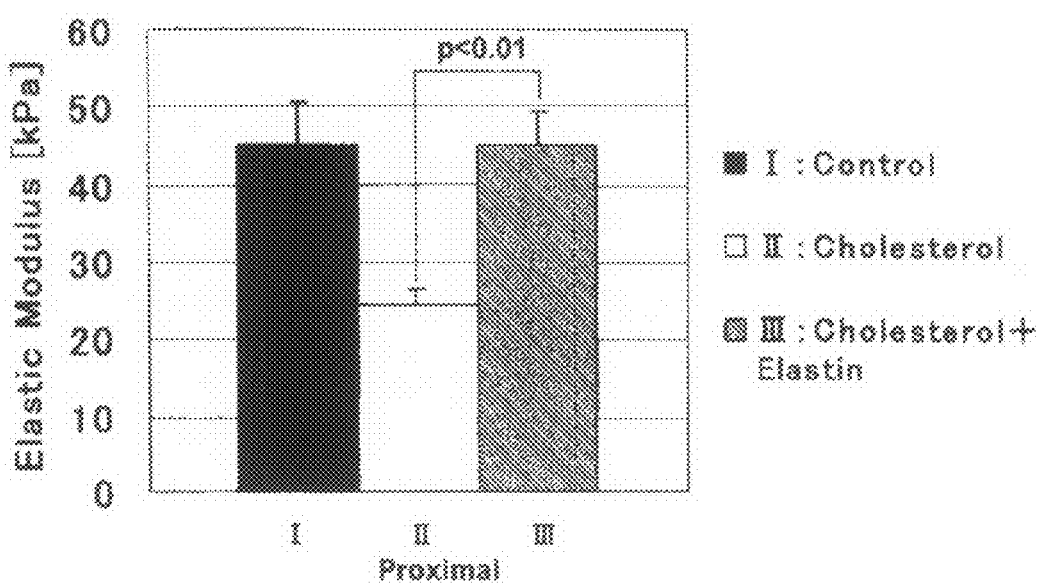

The area around the aorta (heart side) of the rabbit subjected to the experiment was cut at a width of 5 mm, opposite ends of the sample piece were clamped and elongated at a constant speed V of 0.01 mm/s, an average longitudinal elastic modulus in a strain range of 0 to 0.1 was determined as an elastic modulus, and a comparison was carried out between the control group to which the ordinary diet was administered, the cholesterol group to which the cholesterol diet was administered, and the combined cholesterol+elastin group to which were simultaneously administered the cholesterol diet and the water-soluble elastin. The results are as shown in FIG. 8, and it was found that administration of the water-soluble elastin recovered degraded vascular elastic function.

Effect in Suppressing Atheromatous Plague Vascular Lesions

Figure 9:
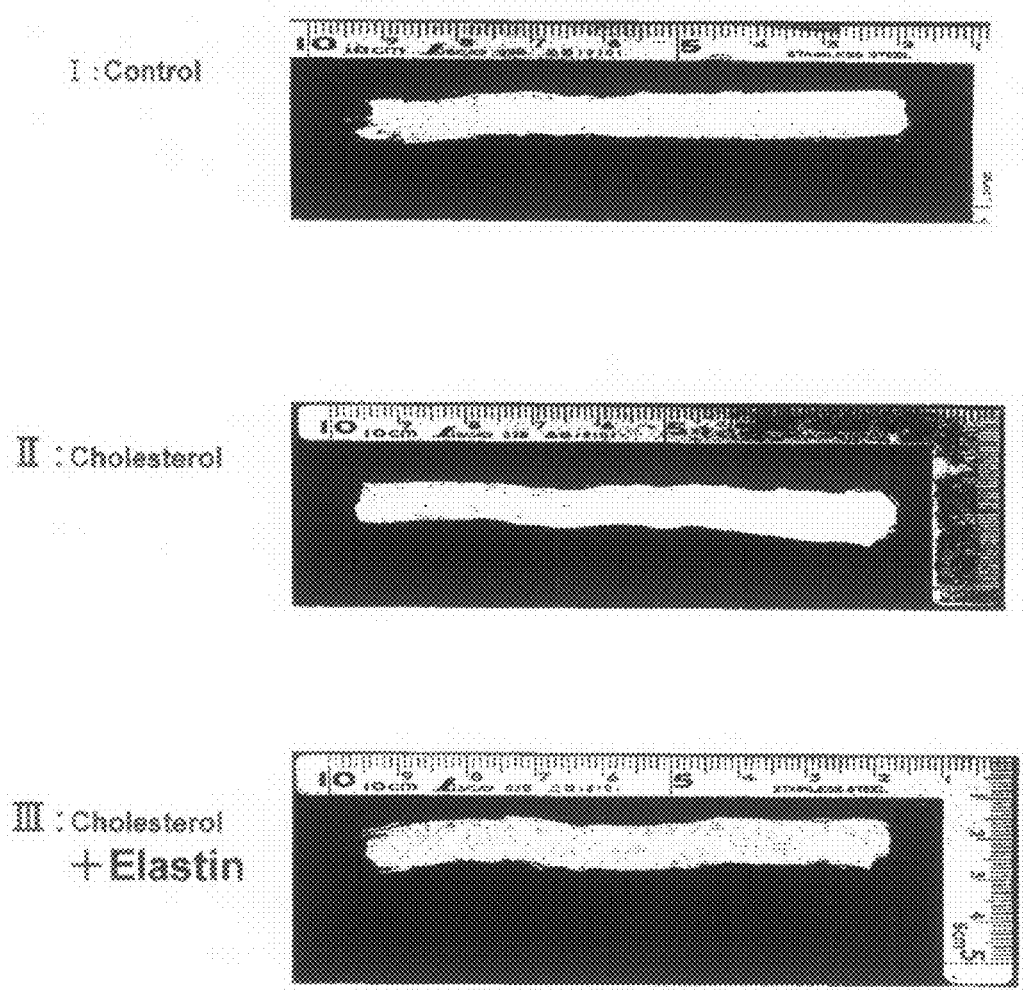

FIG. 9 shows photographs of the surface of the inner membrane of a blood vessel on the blood flow side. For the cholesterol group to which the cholesterol diet was administered, atheromatous plaque (a swollen state in which the blood vessel inner membrane thickens and lipid (cholesterol, etc.) is deposited so as to form atheromatous material, and the surface of the inner membrane is covered with a fibrous coating. When this state progresses, the swelling increases thus preventing blood flow, very narrow blood vessels such as the coronary artery are blocked, and cardiac infarction occurs) was observed all over the surface of the inner membrane (swollen, white appearance). For the combined cholesterol+elastin group fed simultaneously with the cholesterol diet and water-soluble elastin, only a small amount of atheromatous plaque was observed scattered over the surface of the inner membrane. That is, it was found from these three photographs that administration of the water-soluble elastin enabled vascular lesions such as atheromatous plaque to be suppressed.

Effect in Suppressing Thrombogenesis

Thrombus is formed when platelets aggregate in blood. An experiment to inhibit platelet aggregation by water-soluble elastin was carried out in vitro. The low-molecular-weight water-soluble elastin inhibited platelet aggregation by ADP (adenosine-5'-diphosphoric acid), thrombin, or collagen and, in particular, most strongly inhibited platelet aggregation by collagen. The results are given in FIG. 10.

Blood Viscosity

Since, when the concentration of a lipid such as cholesterol in blood increases or platelets adhere/aggregate, the blood viscosity increases and the blood becomes viscous, the viscosity within the blood was measured. The results are given in FIG. 11. It was found that the blood viscosity, which had been increased by administration of cholesterol, was improved by administration of water-soluble elastin.

INDUSTRIAL APPLICABILITY

In accordance with the present invention, a low-molecular-weight high-purity water-soluble elastin and a high-molecular-weight high-purity water-soluble elastin can be obtained. The low-molecular-weight water-soluble elastin of the present invention has high digestive absorption, and can therefore be used as a functional food or as various types of medicine. Furthermore, it can be expected that the high-molecular-weight elastin will find application in a tissue engineering scaffold for regenerative medicine and a coacervate of the high-molecular-weight water-soluble elastin will find application in a cosmetic base for moisturizing since it has a moisture content of 60% to 70%.

What is claimed is:

1. A low-molecular-weight water-soluble elastin having a molecular weight of about 10,000 to 30,000 daltons, purified from a dissolved-elastin solubilizing liquid obtained by dissolving an insoluble elastin obtained from animal body tissue in an aqueous solution of one or more alkali compounds selected from the group consisting of sodium hydroxide, potassium hydroxide, calcium hydroxide, and barium hydroxide, 79% to 84% of the constituent amino acids of the elastin comprising proline, glycine, alanine, and valine, 2% to 3% comprising aspartic acid and glutamic acid, 0.7% to 1.3% comprising lysine, histidine, and arginine, and 0.2% to 0.4% comprising desmosine and isodesmosine.

2. A process for producing a water-soluble elastin from animal body tissue, the process comprising (1) a step of obtaining an insoluble elastin by subjecting the animal body tissue to a collagen removal treatment, (2) a step of obtaining a dissolved-elastin solubilizing liquid by dissolving the insoluble elastin in a solubilizing liquid, and (3) a step of separating the dissolved-elastin solubilizing liquid into two layers by adjusting the temperature to 30° C. to 50° C., recovering a low-molecular-weight water-soluble elastin from the upper layer, and recovering a high-molecular-weight water-soluble elastin from the lower layer,
wherein the low-molecular-weight water-soluble elastin has a molecular weight of about 10,000 to 30,000 daltons and the high-molecular-weight water-soluble elastin has a molecular weight of about 30,000 to 300,000 daltons.

3. The process for producing a water-soluble elastin according to claim 2, wherein the collagen removal treatment is a treatment in which the animal body tissue is immersed in an alkaline solution containing, per liter of solution, 0.05 to 0.5 mole of one or more alkali compounds selected from the group consisting of sodium hydroxide, potassium hydroxide, calcium hydroxide, and barium hydroxide at 90° C. to 105° C. for 10 to 20 minutes.

4. The process for producing a water-soluble elastin according to claim 2, wherein prior to the collagen removal treatment, an immersion treatment is carried out in which the animal body tissue is immersed in a salt solution containing, per liter of solution, 0.1 to 2 mole of one or more salts selected from the group consisting of sodium chloride, potassium chloride, calcium chloride, and barium chloride at 2° C. to 10° C. for 12 to 48 hours.

5. The process for producing a water-soluble elastin according to claim 2, wherein the solubilizing liquid is an alkaline solution containing, per b liter of solution, 0.05 to 0.5 mole of one or more alkali compounds selected from the group consisting of sodium hydroxide, potassium hydroxide, calcium hydroxide, and barium hydroxide at a solution temperature of 90° C. to 105° C.

6. A process for producing a water-soluble elastin from animal body tissue, the process comprising (1) a step of pretreating the animal body tissue, (2) a step of carrying out alkali extraction by immersing the pretreated animal body tissue in an alkaline solution and removing a solution containing collagen and other unwanted protein extracted from the animal body tissue, (3) a step of carrying out alkali dissolution by dissolving the animal body tissue residue, after repeating the operation of (2) above, so as to recover a solution containing a freed water-soluble elastin, and (4) a step of separating the solution containing the water-soluble elastin recovered in the alkali dissolution step into two layers by adjusting the temperature to 30° C. to 50° C., recovering a low-molecular-weight water-soluble elastin from the upper layer, and recovering a high-molecular-weight water-soluble elastin from the lower layer,
wherein the low-molecular-weight water-soluble elastin has a molecular weight of about 10,000 to 30,000 daltons and the high-molecular-weight water-soluble elastin has a molecular weight of about 30,000 to 300,000 daltons.

7. The process for producing a water-soluble elastin according to claim 6, wherein the alkali extraction step comprises immersing the pretreated animal body tissue in an alkaline solution containing, per b liter of solution, 0.05 to 0.5 mole of one or more alkali compounds selected from the group consisting of sodium hydroxide, potassium hydroxide, calcium hydroxide, and barium hydroxide at 90° C. to 105° C. for 10 to 20 minutes.

8. The process for producing a water-soluble elastin according to claim 6, wherein the alkali dissolution step comprises immersing the animal body tissue residue treated in the alkali extraction step in an alkaline solution containing, per b liter of solution, 0.05 to 0.5 mole of one or more alkali compounds selected from the group consisting of sodium hydroxide, potassium hydroxide, calcium hydroxide, and barium hydroxide at 90° C. to 105° C. for 20 to 240 minutes.

9. The process for producing a water-soluble elastin according to claim 6, wherein the pretreatment step comprises at least one of a treatment for removing unwanted portions of the animal body tissue, a treatment for finely cutting the animal body tissue, and a treatment for delipidating the animal body tissue.

10. A functional food comprising a low-molecular-weight water-soluble elastin having a molecular weight of about 10,000 to 30,000 daltons, purified from a dissolved-elastin solubilizing liquid obtained by dissolving an insoluble elastin obtained from animal body tissue in an aqueous solution of one or more alkali compounds selected from the group consisting of sodium hydroxide, potassium hydroxide, calcium hydroxide, and barium hydroxide, 79% to 84% of the constituent amino acids of the elastin comprising proline, glycine, alanine, and valine, 2% to 3% comprising aspartic acid and glutamic acid, 0.7% to 1.3% comprising lysine, histidine, and arginine, and 0.2% to 0.4% comprising desmosine and isodesmosine.

11. The functional food according to claim 10, wherein the food further comprises a metal useful to a living body in addition to the low-molecular-weight water-soluble elastin.

12. A medicine comprising as an active ingredient a low-molecular-weight water-soluble elastin having a molecular weight of about 10,000 to 30,000 daltons, purified from a dissolved-elastin solubilizing liquid obtained by dissolving an insoluble elastin obtained from animal body tissue in an aqueous solution of one or more alkali compounds selected from the group consisting of sodium hydroxide, potassium hydroxide, calcium hydroxide, and barium hydroxide, 79% to 84% of the constituent amino acids of the elastin comprising proline, glycine, alanine, and valine, 2% to 3% comprising aspartic acid and glutamic acid, 0.7% to 1.3% comprising lysine, histidine, and arginine, and 0.2% to 0.4% comprising desmosine and isodesmosine.

13. The medicine according to claim 12, wherein the medicine further comprises a metal useful to a living body in addition to the low-molecular-weight water-soluble elastin.

14. The medicine according to claim 12, wherein the medicine is an antiarteriosclerotic agent.

15. The medicine according to claim 12, wherein the medicine is a lipidosis improving agent.

16. The medicine according to claim 12, wherein the medicine is an antithrombogenic agent.

* * * * *